(12) United States Patent
Ouellette et al.

(10) Patent No.: US 7,022,846 B2
(45) Date of Patent: Apr. 4, 2006

(54) METABOLITES OF PRINOMASTAT AND THEIR SYNTHESIS

(75) Inventors: Michael A. Ouellette, San Diego, CA (US); Barbara C. M. Potts, Escondido, CA (US); Jayaram K. Srirangam, San Diego, CA (US); Anthony R. Tibbetts, San Diego, CA (US); Kanyin E. Zhang, San Diego, CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 10/458,510

(22) Filed: Jun. 10, 2003

(65) Prior Publication Data

US 2004/0053922 A1 Mar. 18, 2004

Related U.S. Application Data

(60) Provisional application No. 60/387,548, filed on Jun. 10, 2002.

(51) Int. Cl.
*C07D 417/12* (2006.01)
*A61K 31/541* (2006.01)

(52) U.S. Cl. ..................................... 544/58.4; 436/92
(58) Field of Classification Search ............... 544/58.4; 514/227.8
See application file for complete search history.

(56) References Cited

U.S. PATENT DOCUMENTS

| 5,183,900 A | 2/1993 | Galardy et al. |
| 5,189,178 A | 2/1993 | Galardy et al. |
| 5,455,258 A | 10/1995 | MacPherson et al. |
| 5,506,242 A | 4/1996 | MacPherson et al. |
| 5,552,419 A | 9/1996 | MacPherson et al. |
| 5,753,653 A | 5/1998 | Bender et al. |
| 6,153,757 A | 11/2000 | Zook et al. |

FOREIGN PATENT DOCUMENTS

| EP | 0276436 | 8/1988 |
| EP | 0438223 | 7/1991 |
| EP | 0606046 | 7/1994 |
| WO | WO 92/06966 | 4/1992 |
| WO | WO 92/09563 | 6/1992 |
| WO | WO 92/21360 | 12/1992 |
| WO | WO 95/35276 | 12/1995 |
| WO | WO 96/00214 | 1/1996 |
| WO | WO 96/27583 | 9/1996 |
| WO | WO 97/20824 | 6/1997 |
| WO | WO 00/04982 | * 2/2000 |

OTHER PUBLICATIONS

STN search printout (Jul. 26, 2004).*
Coussens et al. {SCIENCE vol. 295, Mar. 29, pp. 2387-2392, (2002)}.*
Skiles et al. {Current Medicinal Chemistry, 8, 425-474 (2001)}.*
Roomi MW et al. "A Novel in Vitro Bioassay for Screening Matrix Metalloproteinase Activity in Human Cancer Cell Lines (2003)" http://www.drrathresearch.org/lab_research/study_c_a_novel_invitro.html downloaded on Apr. 20, 2005.*
Beckett, et. al., "Recent Advances in Matrix Metalloproteinase Inhibitor Research," *Drug Discovery Today*, 1996, 16-26, vol. 1, No. 1.
Davies, et. al., "A Synthetic Matrix Metalloproteinase Inhibitor Decreases Tumor Burden and Prolongs Survival of Mice Bearing Human Ovarian Carcinoma Xenografts," *Cancer Research*, 1993, 2087-2091, vol. 53.
Harrison et. al., "A Semicontinuous, High-Performance Liquid Chromatography-Based Assay for Stromelysin," *Analytical Biochemistry*, 1989, 110-113, 180.
Johnson, et. al., "Collagenase Inhibitors: Their Design and Potential Therapeutic Use," *Journal of Enzyme Inhibition*, 1987, 1-22, 2.
Morphy, et. al., "Matrix Metalloproteinase Inhibitors: Current Status," *Current Medicinal Chemistry*, 1995, 743-762, 2.
Porter, et. al., "Recent Developments In Matrix Metalloproteinase Inhibitors," *Exp. Opin. Ther. Patents*, 1995, 1287-1296, vol. 5, No. 12.
Pretsch, et. al., *Spectral Data for Structure Determination of Organic Compounds*, 1989, Springer-Verlag, 2$^{nd}$ Edition.

(Continued)

*Primary Examiner*—Mark L Berch
*Assistant Examiner*—Kahsay Habte
(74) *Attorney, Agent, or Firm*—Ye Hua; Stephan D. Prodnuk; Bryan C. Zielinski

(57) ABSTRACT

Metabolites of a matrix metalloproteinase inhibitor prinomastat and their synthesis. These metabolites are: (3S)-N-hydroxy-4-(4-((1-oxy-pyrid-4-yl)oxy)benzenesulfonyl)-2,2-dimethyl-tetrahydro-2H-1,4-thiazine-3-carboxamide (M6); (3S)-2,2-dimethyl-1,1-dioxo-4-[4-(1-oxy-pyridin-4-yloxy)-benzenesulfonyl]-thiomorpholine-3-carboxylic acid amide (M7); (3S)-2,2-dimethyl-4-[4-(1-oxypyridin-4-yloxy)-benzenesulfonyl]-thiomorpholine-3-carboxylic acid amide (M8); (3S)-2,2-dimethyl-1,1-dioxo-4-[4-(pyridin-4-yloxy)-benzenesulfonyl]-thiomorpholine-3-carboxylic acid amide (M2); and (3S)-2,2-dimethyl-4-[4-(pyridin-4yloxy)-benzenesulfonyl)-thiomorphpline-3-carboxylic acid amide (M3).

26 Claims, 1 Drawing Sheet

OTHER PUBLICATIONS

*Remington's Pharmaceutical Sciences*, 1990, 18th Edition, Easton, Pennsylvania.

Schmidt, et. al., "Resonance Raman Investigation of β-(2-Furyl)-Acryloyl-Glyceraldehyde-3-Phosphate Dehydrogenase," *FEBS Letters*, 1978, 263-268, vol. 96, No. 2.

Smallcombe, et. al., "WET Solvent Suppression and Its Applications to LC NMR and High-Resolution NMR Spectroscopy," *Journal of Magnetic Resonance, Series A*, 1995, 295-303, 117.

Still, et. al., "Rapid Chromatographic Technique for Preparative Separations with Moderate Resolution," *Journal of Organic Chemistry*, 1978, 2923-2925, 43, No. 14.

Swartz, et. al., "8 Synthetic Inhibitors of Bacterial and Mammalian Interstitial Collagenases," *Progress in Medicinal Chemistry*, 1992, 271-334, 29.

Weingarten, et. al., "Spectrophotometric Assay For Vertebrate Collagenase," *Analytical Biochemistry*, 1985, 437-440, 147.

* cited by examiner

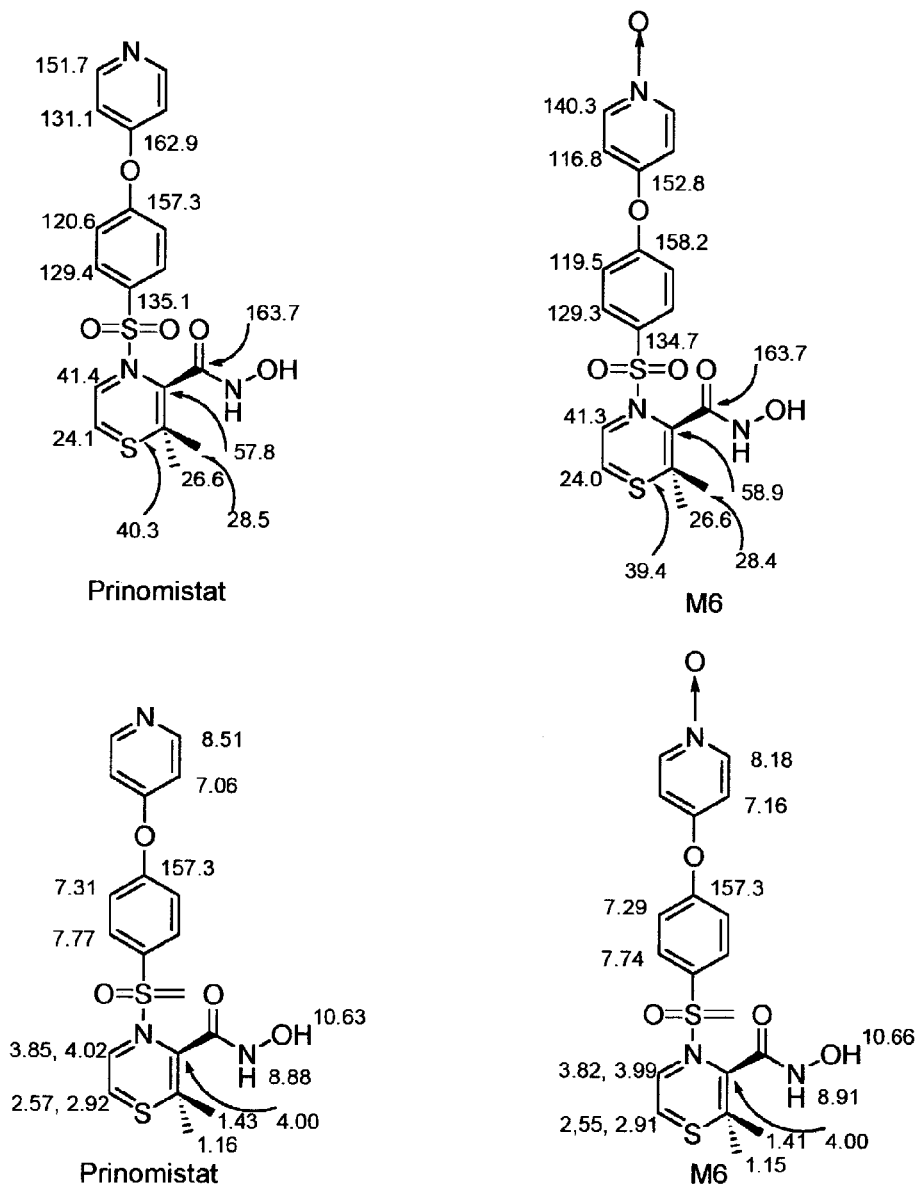
Figure 1. $^{13}C$ Chemical shifts of prinomastat (top left) and M6 (top right) in DMSO-$d_6$
$^1H$ Chemical shifts of prinomastat (bottom left) M6 (bottom right) in DMSO-$d_6$

METABOLITES OF PRINOMASTAT AND THEIR SYNTHESIS

The present patent application claims priority to U.S. Ser. No. 60/387,548, filed Jun. 10, 2002, which is hereby incorporated by reference in its entirety for all purposes.

TECHNICAL FIELD AND INDUSTRIAL APPLICABILITY OF THE INVENTION

This invention relates to metabolites of (3S)-N-hydroxy-4-(4-(pyrid-4-yloxy)benzenesulfonyl)-2,2-dimethyl-tetrahydro-2H-1,4-thiazine-3-carboxamide, a matrix metalloproteinase inhibitor having the generic name Prinomistat, and to their synthesis.

BACKGROUND OF THE INVENTION

Matrix metalloproteinases ("MMPs") are a family of enzymes, including, collagenases, gelatinases, matrilysin, and stromelysins, that are involved in the degradation and remodeling of connective tissues. These enzymes are contained in a number of cell types that are found in or are associated with connective tissue, such as fibroblasts, monocytes, macrophages, endothelial cells and metastatic tumor cells. They also share a number of properties, including zinc and calcium dependence, secretion as zymogens, and, 40–50% amino acid sequence homology.

Matrix metalloproteinases degrade the protein components of the extracellular matrix, i.e., the protein components found in the linings of joints, interstitial connective tissue, basement membranes, cartilage and the like. These proteins include collagen, proteoglycan, fibronectin and lamanin.

In a number of pathological disease conditions, however, deregulation of matrix metalloproteinase activity leads to the uncontrolled breakdown of extracellular matrix. These disease conditions include arthritis (e.g., rheumatoid arthritis and osteoarthritis), periodontal disease, aberrant angiogenesis, tumor metastasis and invasion, tissue ulceration (e.g., corneal ulceration, gastric ulceration or epidermal ulceration), bone disease, HIV-infection and complications from diabetes.

Administration of matrix metalloproteinase inhibitors has been found to reduce the rate of connective tissue degradation, thereby leading to a favorable therapeutic effect. For example, in *Cancer Res.*, 53, 2087 (1993), a synthetic matrix metalloproteinase inhibitor was shown to have in vivo efficacy in a murine model for ovarian cancer with an apparent mode of action consistent with inhibition of matrix remodeling. The design and uses of MMP inhibitors are reviewed, for example, in *J. Enzyme Inhibition*, 2, 1–22 (1987); *Progress in Medicinal Chemistry*, 29, 271–334 (1992); *Current Medicinal Chemistry*, 2, 743–762 (1995); *Exp. Opin. Ther. Patents*, 5, 12871296 (1995); and *Drug Discovery Today*, 1, 16–26 (1996).

Matrix metalloproteinase inhibitors are also the subject of numerous patents and patent applications, including: U.S. Pat. Nos. 5,189,178; 5,183,900; 5,506,242; 5,552,419; and 5,455,258; European Patent Application Nos. EP 0 438 223 and EP 0 276 436; International Publication Nos. WO 92/21360; WO 92/06966; WO 92/09563; WO 96/00214; WO 95/35276; and WO 96/27583.

Further, U.S. Pat. Nos. 6,153,757 and 5,753,653 relate to prinomistat and its synthesis, the disclosures of each are incorporated herein by reference in their entireties.

Prinomastat, shown below, is a potent inhibitor of certain metalloproteinases (MMP), particularly matrix metalloproteinases and tumor necrosis factor-α convertase. International Publication No. WO 97/208824 discloses the chemical structure of prinomistat, its pharmaceutical composition, as well as pharmaceutical uses, methods of its preparation and intermediates useful in its synthesis.

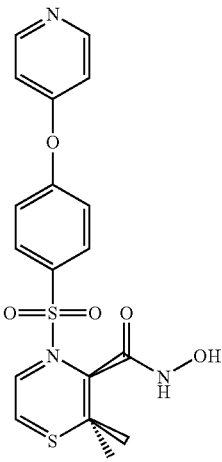

Until now, metabolites of prinomastat have not been identified, isolated, purified or synthesized. Further, it is shown that some of these metabolites are potent matrix metalloproteinase inhibitors.

SUMMARY OF THE INVENTION

The present invention is directed to certain metabolites of prinomastat and their synthesis; namely: (3S)-N-hydroxy-4-(4-((1-oxy-pyrid-4-yl)oxy)benzenesulfonyl)-2,2-dimethyl-tetrahydro-2H-1,4-thiazine-3-carboxamide (M6); (3S)-2,2-dimethyl-1,1-dioxo-4-[4-(1-oxy-pyridin-4-yloxy)-benzenesulfonyl]-thiomorpholine-3-carboxylic acid amide (M7); (3S)-2,2-dimethyl-4-[4-(1-oxy-pyridin-4-yloxy)-benzenesulfonyl]-thiomorpholine-3-carboxylic acid amide (M8); (3S)-2,2-dimethyl-1,1-dioxo-4-[4-(pyridin-4-yloxy) benzenesulfonyl]-thiomorpholine-3-carboxylic acid amide (M2); and (3S)-2,2-dimethyl-4-[4-(pyridin-4yloxy)-benzenesulfonyl)-thiomorpholine-3-carboxylic acid amide (M3). Particularly preferred is the isolated or substantially pure form of metabolites M6, M7, M8, M2, and M3, or a mixture thereof.

One preferred embodiment of the invention is substantially pure N-hydroxy-4-(4-((1-oxy-pyrid-4-yl)oxy)benzenesulfonyl)-2,2-dimethyl-tetrahydro-2H-1,4-thiazine-3-carboxamide having the following structure

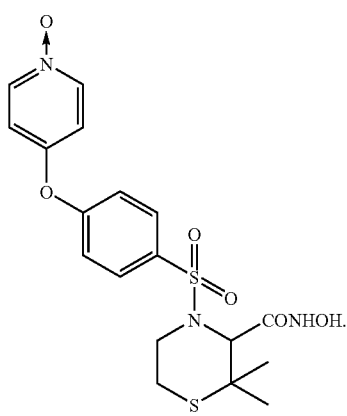

More preferably the compound of formula 11 is 95% pure, even more preferably the compound of formula 11 is 98% pure.

Another preferred embodiment is substantially pure (3S)-N-hydroxy-4-(4-((1-oxy-pyrid-4-yl)oxy)benzenesulfonyl)-2,2-dimethyl-tetrahydro-2H-1,4-thiazine-3-carboxamide having the following structure

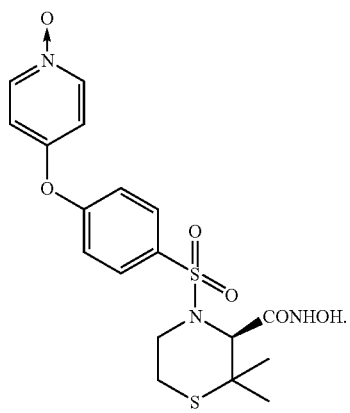
22

More preferably the compound of formula 22 is 95% pure, even more preferably the compound of formula 22 is 98% pure.

Another preferred embodiment of the invention is a process for synthesizing a compound of formula 11, N-hydroxy-4-(4-((1-oxy-pyrid-4-yl)oxy)benzenesulfonyl)-2,2-dimethyl-tetrahydro-2H-1,4-thiazine3-carboxamide, including the steps of:

(i) protecting a compound of formula 1

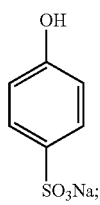
1 with a protecting group, $P_1$, to form a compound of formula 2

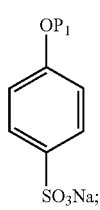
2

(ii) activating the compound of formula 2 with an activating agent, $A_1$, to form a compound of formula 3

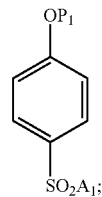
3

(iii) coupling the compound of formula 3 with a compound of formula 4 having an ester, $E_1$

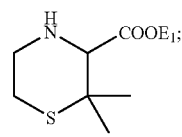
4 to form a compound of formula 5

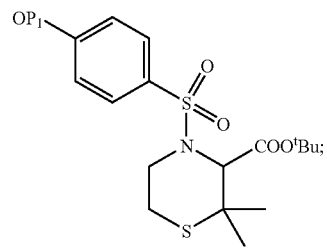
5

(iv) removing the protecting group, $P_1$, from the compound of formula 5 to form a compound of formula 6

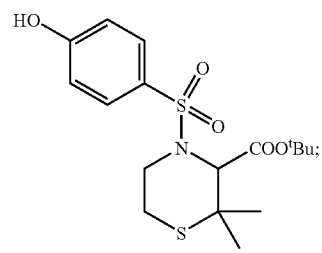
6

(v) coupling the compound of formula 6 with p-nitro pyridine N-oxide, a compound of formula 7

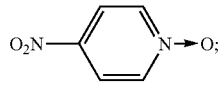
7 to form a compound of formula 8

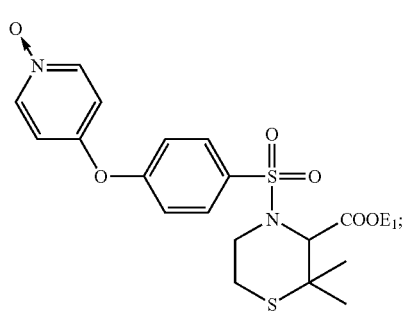

(vi) removing the ester, $E_1$, from the compound of formula 8 to form a compound of formula 9

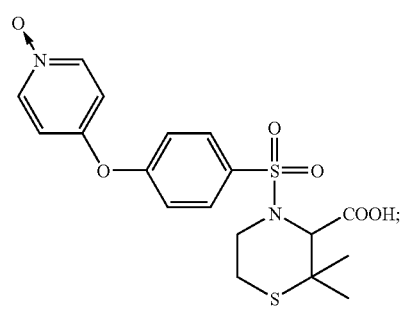

(vii) activating the compound of formula 9 with an activating agent, $A_2$, to form a compound of formula 10

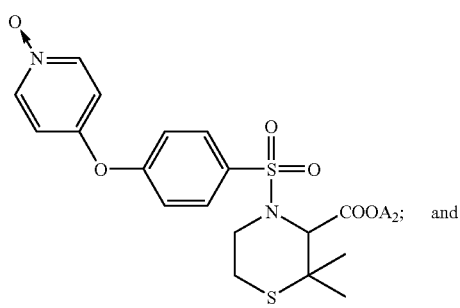

(viii) treating the compound of formula 10 with hydroxylamine to form the compound of formula 11

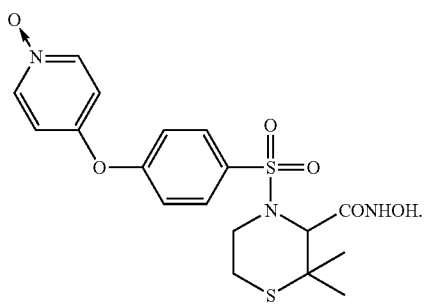

More preferably, the compound of formula 9

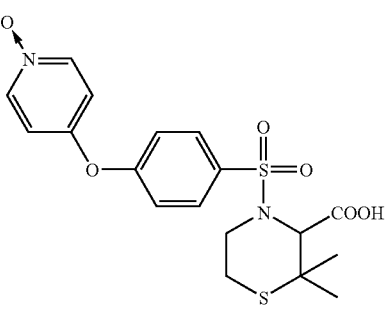

is converted to the compound of formula 11

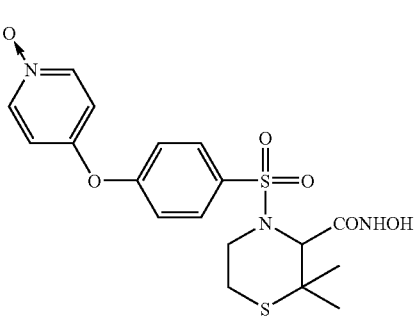

by using an N-protected hydroxylamine and a fluoride based resin as an ion exchanger. Even more preferably, the phenolic group is protected in step (i) above by treatment with an acetic anhydride in the presence of pyridine; the activating agent, $A_1$, in step (ii) above is thionyl chloride and performed under refluxing conditions; the ester, $E_1$, of 2,2-dimethyl-thiomorpholine-3-carboxylic acid is a tert-butyl ester, $P_1$, is removed in step (vi) above by a treatment with potassium carbonate in aqueous methanol; the coupling in step (v) above is conducted in dimethylformamide in the presence of potassium carbonate; the ester group in step (vi) above is removed by a treatment with a trifluoroacetic acid in dichloromethane in the presence of anisole; the compound of formula 9 in step (vii) above is activated by a reaction with thionyl chloride.

Another preferred embodiment of the invention is a process for synthesizing a compound of formula 22, (3S)-N-hydroxy-4-(4-((1-oxy-pyrid-4-yl)oxy)benzenesulfonyl)-2,2-dimethyl-tetrahydro-2H-1,4-thiazine-3-carboxamide, including the steps of:

(i) protecting a compound of formula 12

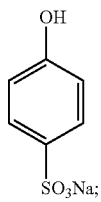

with a protecting group, $P_1$, to form a compound of formula 13

13

[Structure: 4-(OP$_1$)-C$_6$H$_4$-SO$_3$Na]

(ii) activating the compound of formula 13 with an activating agent, $A_1$, to form a compound of formula 14

14

[Structure: 4-(OP$_1$)-C$_6$H$_4$-SO$_2$A$_1$]

(iii) coupling the compound of formula 14 with a compound of formula 15 having an ester, $E_1$

15

[Structure: thiomorpholine with gem-dimethyl and COOE$_1$ substituent, NH]

to form a compound of formula 16

16

[Structure: 4-(OP$_1$)-phenyl sulfonyl attached to N of gem-dimethyl thiomorpholine with COO$^t$Bu]

(iv) removing the protecting group, $P_1$, from the compound of formula 16 to form a compound of formula 17

17

[Structure: 4-HO-phenyl sulfonyl attached to N of gem-dimethyl thiomorpholine with COO$^t$Bu]

(v) coupling the compound of formula 17 with p-nitro pyridine N-oxide, a compound of formula 18

18

[Structure: $O_2N$-pyridine-N→O]

to form a compound of formula 19

19

[Structure: pyridine N-oxide-O-phenyl-sulfonyl-N-(gem-dimethyl thiomorpholine)-COOE$_1$]

(vi) removing the ester, $E_1$, from the compound of formula 19 to form a compound of formula 20

20

[Structure: pyridine N-oxide-O-phenyl-sulfonyl-N-(gem-dimethyl thiomorpholine)-COOH]

(vii) activating the compound of formula 20 with an activating agent, $A_2$, to form a compound of formula 21

21

[Structure: pyridine N-oxide-O-phenyl-sulfonyl-N-(gem-dimethyl thiomorpholine)-COOA$_2$]

(viii) treating the compound of formula 21 with hydroxylamine to form the compound of formula 22

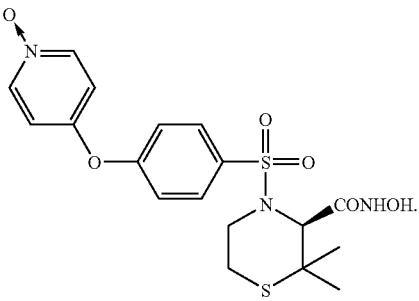

More preferably, the compound of formula 20

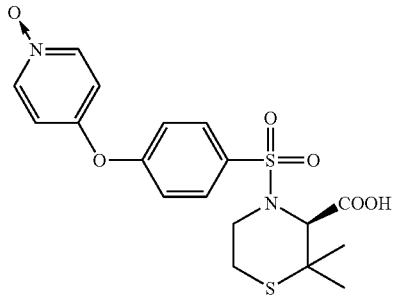

is converted to the compound of formula 22

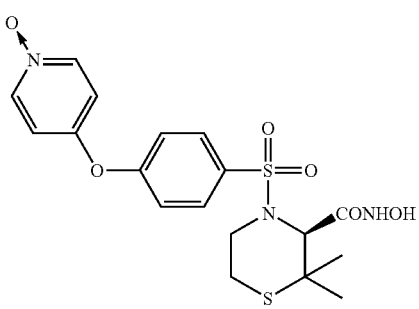

by using an N-protected hydroxylamine and a fluoride based resin as an ion exchanger. Even more preferably, the phenolic group is protected in step (i) above by treatment with an acetic anhydride in the presence of pyridine; the activating agent, $A_1$, in step (ii) above is thionyl chloride and performed under refluxing conditions; the ester, $E_1$, of 2,2-dimethyl-thiomorpholine-3(S)-carboxylic acid is a tert-butyl ester; $P_1$, is removed in step (vi) above by a treatment with potassium carbonate in aqueous methanol; the coupling in step (v) above is conducted in dimethylformamide in the presence of potassium carbonate; the ester group in step (vi) above is removed by a treatment with a trifluoroacetic acid in dichloromethane in the presence of anisole; the compound of formula 20 in step (vii) above is activated by a reaction with thionyl chloride.

Another preferred embodiment is a method for synthesizing 2,2-dimethyl-1,1-dioxo-4-[4-(1-oxy-pyridin-4-yloxy)-benzenesulfonyl]-thiomorpholine-3-carboxylic acid amide including the steps of:
(i) converting N-hydroxy-4-(4-((1-oxy-pyrid-4-yl)oxy)benzenesulfonyl)-2,2-dimethyl-tetrahydro-2H-1,4-thiazine-3-carboxamide to a corresponding acid amide; and
(ii) oxidizing the corresponding acid amide.

More preferably the corresponding acid is 2-dimethyl-4-[4-(1-oxypyridin-4-yloxy)-benzenesulfonyl]-thiomorpholine-3-carboxylic acid amide amide is oxidized with peracetic acid.

Another preferred embodiment is a method for synthesizing (3S)-2,2-Dimethyl-1,1-dioxo-4-[4-(1-oxy-pyridin-4-yloxy)-benzenesulfonyl]-thiomorpholine-3-carboxylic acid amide including the steps of:
(i) converting (3S)-N-hydroxy-4-(4-((1-oxy-pyrid-4-yl)oxy)benzenesulfonyl)-2,2-dimethyl-tetrahydro-2H-1,4-thiazine-3-carboxamide to a corresponding acid amide; and
(ii) oxidizing the corresponding acid amide.

More preferably the corresponding acid amide is (3S)-2,2-dimethyl-4-[4-(1-oxy-pyridin-4-yloxy)-benzenesulfonyl]-thiomorpholine-3-carboxylic acid amide is oxidized with peracetic acid.

Another preferred embodiment is a method of treating a mammalian disease condition mediated by metalloproteinase activity in patients in need of such treatment, said method comprising administering an effective amount of a compound of the formula 11 or 22 to said patient in unit dosage form. More preferably, the mammalian disease condition is tumor growth, invasion or metastasis, or arthritis.

Other aspects, features, and advantages of the invention will become apparent upon consideration of the detailed description below in conjunction with the appended figure.

BRIEF DESCRIPTION OF THE DRAWINGS

FIG. 1 is a comparison of the $^1$H and $^{13}$C chemical shifts of Prinomistat and M6.

DETAILED DESCRIPTION OF THE INVENTION AND IT'S PREFERRED EMBODIMENTS

As used herein, the terms "comprising" and "including" are used in an open, non-limiting, sense.

A. Prinomastat Metabolites and Their Synthesis

This invention relates to certain metabolites of prinomastat (M6, M7, M8, M2, and M3) and their synthesis. The major human circulating metabolite of prinomastat is (3S)-N-hydroxy-4-(4-((1-oxy-pyrid-4-yl)oxy)benzenesulfonyl)-2,2-dimethyl-tetrahydro-2H-1,4-thiazine-3-carboxamide (M6):

(Formula 22)

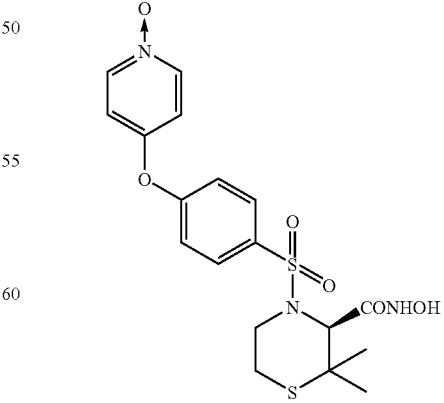

M6

M6 is the pyridine N-oxide analogue of prinomastat, and its product ion mass spectrum shows fragment ions at m/z 129, 186, 187, and 252, which are mass spectrometric features in common with the structure shown for metabolite M6.

Substantially pure as used herein is defined as a compound of greater than 95% purity. Preferably, compounds are of greater than 99% purity.

Synthesis:

The following Reaction Scheme A is a route by which M6 can be prepared from commercially available materials.

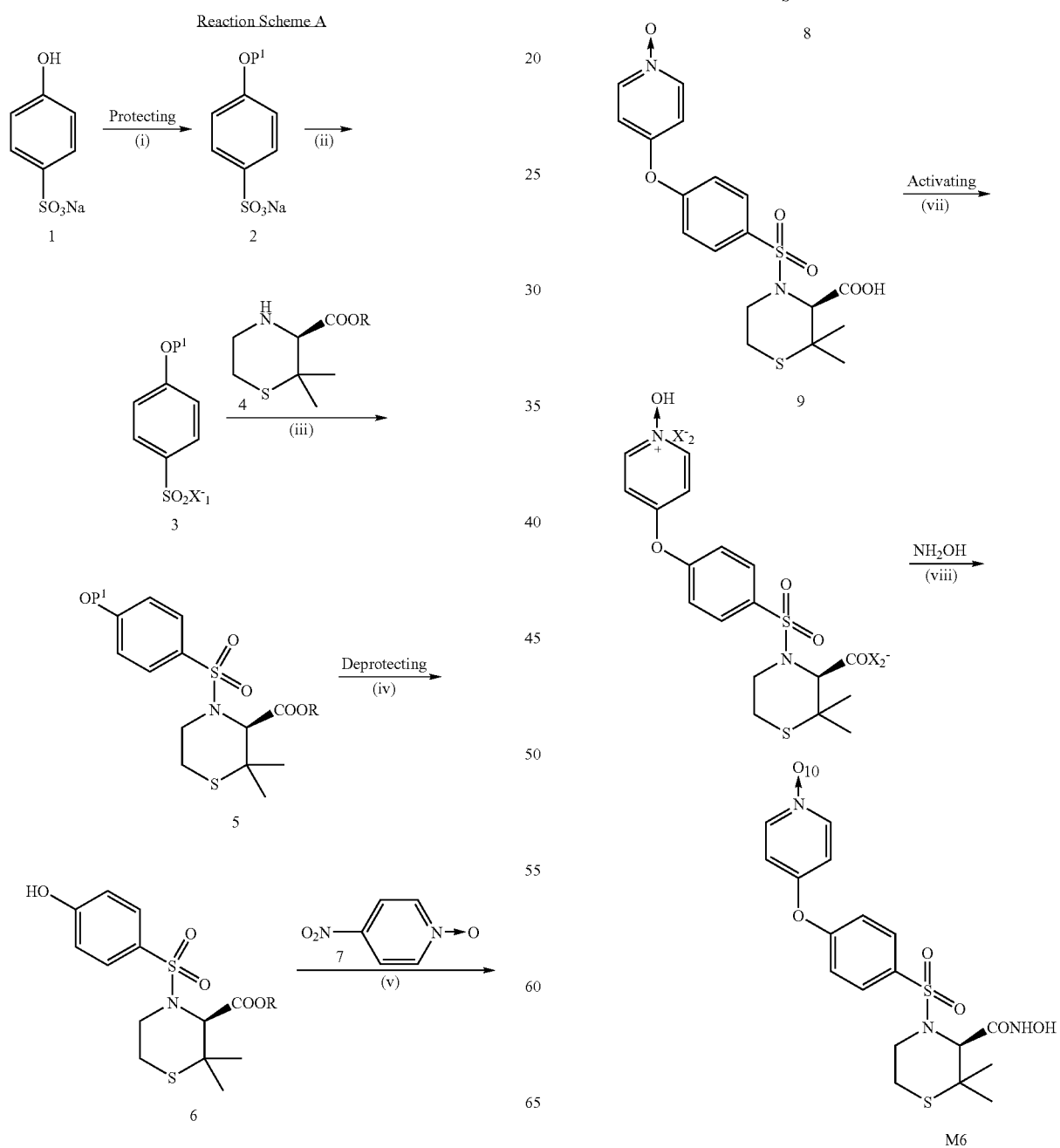

According to Scheme A, M6 was synthesized starting from commercially available p-hydroxy benzenesulfonic acid (compound (1)).

In step (i), the phenolic group of compound (1) is protected by replacing the hydrogen of the hydroxy group with $P^1$, which can be any suitable protecting group, to form compound (2). For example, $P^1$ can be an acetyl group, when compound (1) is treated with acetic anhydride in the presence of pyridine; acetyl chloride/NaOH; acetic anhydride/NaOH; or 1-acetyl-1H-1,2,3-triazolo[4,5-B]pyridine/NaOH.

In step (ii), the sulfonic group of compound (2) is activated to form compound (3). One way to accomplish such an activation is to convert compound (2) into a sulfonyl chloride by a treatment with thionyl chloride under refluxing conditions or by treatment with oxalyl chloride and catalytic dimethylformamide in a suitable aprotic solvent.

In step (iii), compound (3) is coupled with an ester of 2,2-dimethyl-thiomorpholine-3-(S)-carboxylic acid (compound (4)), resulting in a quantitative yield of a sulfonamide, which is compound (5). R in compound (4) can be any suitable protecting group. For example, R can be a tert-butyl ester, or any other ester stable to base.

In step (iv), protecting group $P^1$ is removed to form compound (6). One way to accomplish such a deprotection is to treat compound (5) with potassium carbonate in aqueous methanol; a carbonate or bicarbonate in any aqueous alcohol; or hydroxide of an alkali metal in an alcohol solvent.

In step (v), compound (6) is coupled with p-nitro pyridine N-oxide, compound (7), to form compound (8). This coupling may be accomplished in dimethylformamide (DMF) in the presence of potassium carbonate.

In step (vi), the ester group is removed to convert compound (8) into an acid (compound (9)). This conversion may be accomplished by a treatment with trifluoroacetic acid in dichloromethane in the presence of anisole or by treatment with any other suitable acid.

In step (vii), the carboxyl group of compound (9) is activated, forming compound (10). For example, the carboxyl group can be activated by being converted into an acid chloride via a reaction with thionyl chloride or by treatment with oxalyl chloride and catalytic dimethylformamide in a suitable aprotic solvent. This reaction can be carried out at room temperature.

Finally, in step (viii), compound (10) can be converted to metabolite M6 by treatment with hydroxylamine. This conversion leads to a mixture of compound (9) and M6, which can be separated by, for example, by repeated silica gel column chromatography and precipitation.

To synthesize a racemic mixture of metabolite M6, a racemic mixture of the 2,2-dimethyl-thiomorpholine-3-carboxylic acid ester is used in step (iii).

The following Reaction Scheme 1A shows a preferred embodiment for synthesizing metabolite M6.

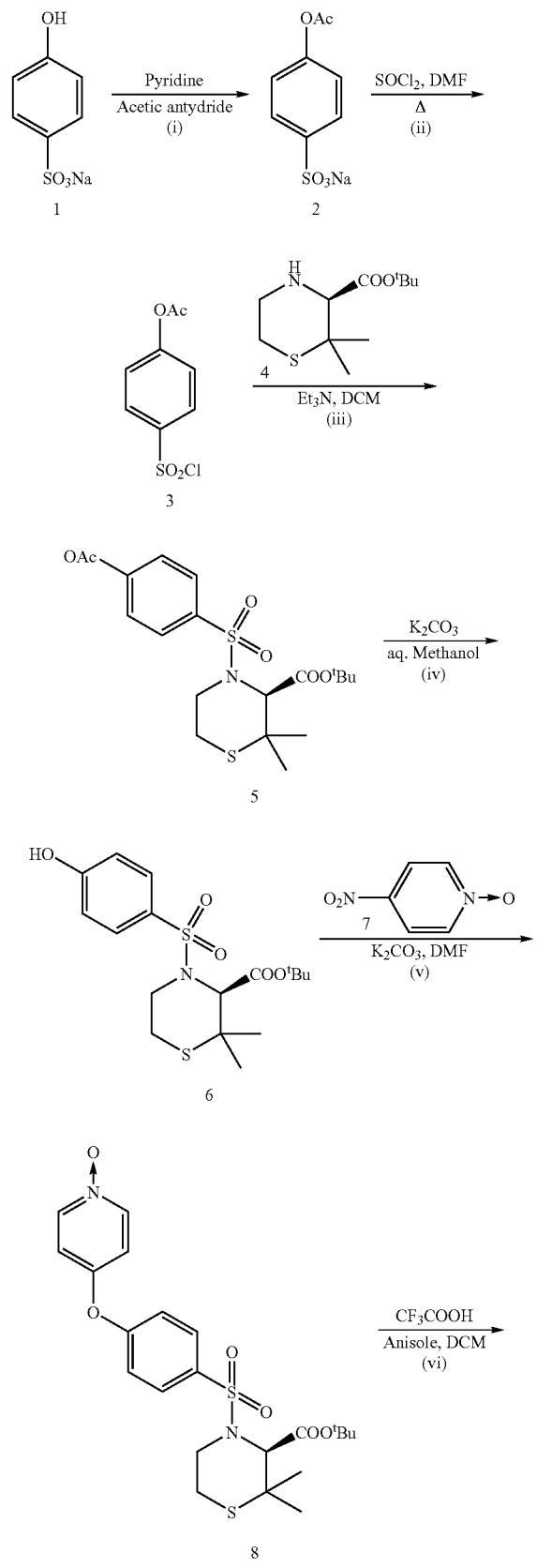

Reaction Scheme 1A

-continued

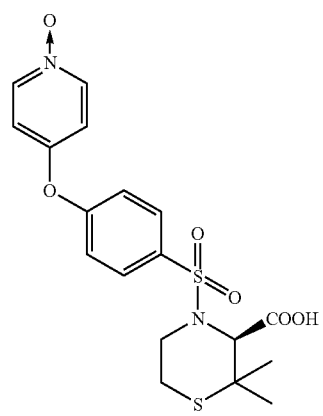

9

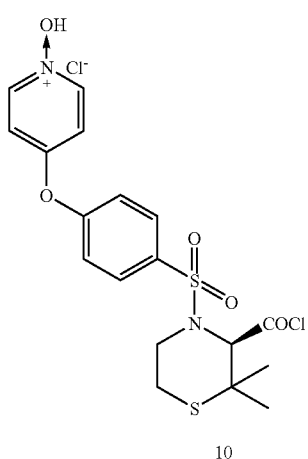

10

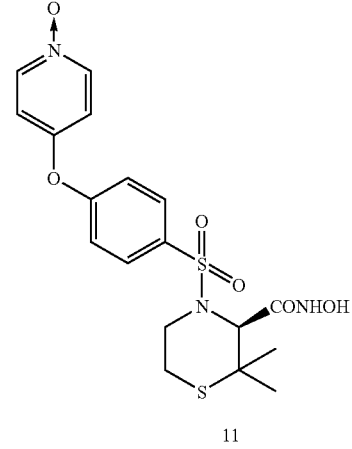

11

To avoid formation of compound (10) in step (vii) in Reaction Scheme 1A, the hydroxymate, compound (9), can be directly converted to metabolite M6 compound (11), through a one-pot synthesis. This conversion is illustrated by Reaction Scheme 1B shown below:

Reaction Scheme 1B

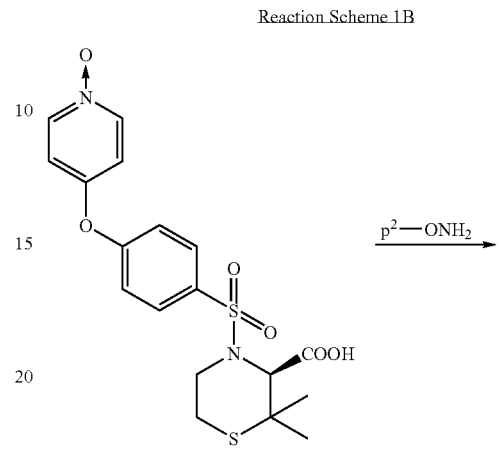

Reaction Scheme 1B involves the use of an N-protected hydroxylamine and a fluoride-based resin as an anion exchanger. $P^2$ in the N-protected hydroxylamine can be any suitable protecting group. Any fluoride-based resin that is a strongly basic anion exchanger can be used. Preferably, such a resin is a fluoride form of Amberlite A-26™, available from, for example, Fluka Chemie AG (USA), which has the following structure:

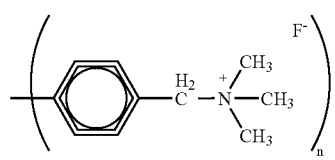

A preferred one-pot synthesis of M6 from compound (9) is shown in the following Reaction Scheme 1C.

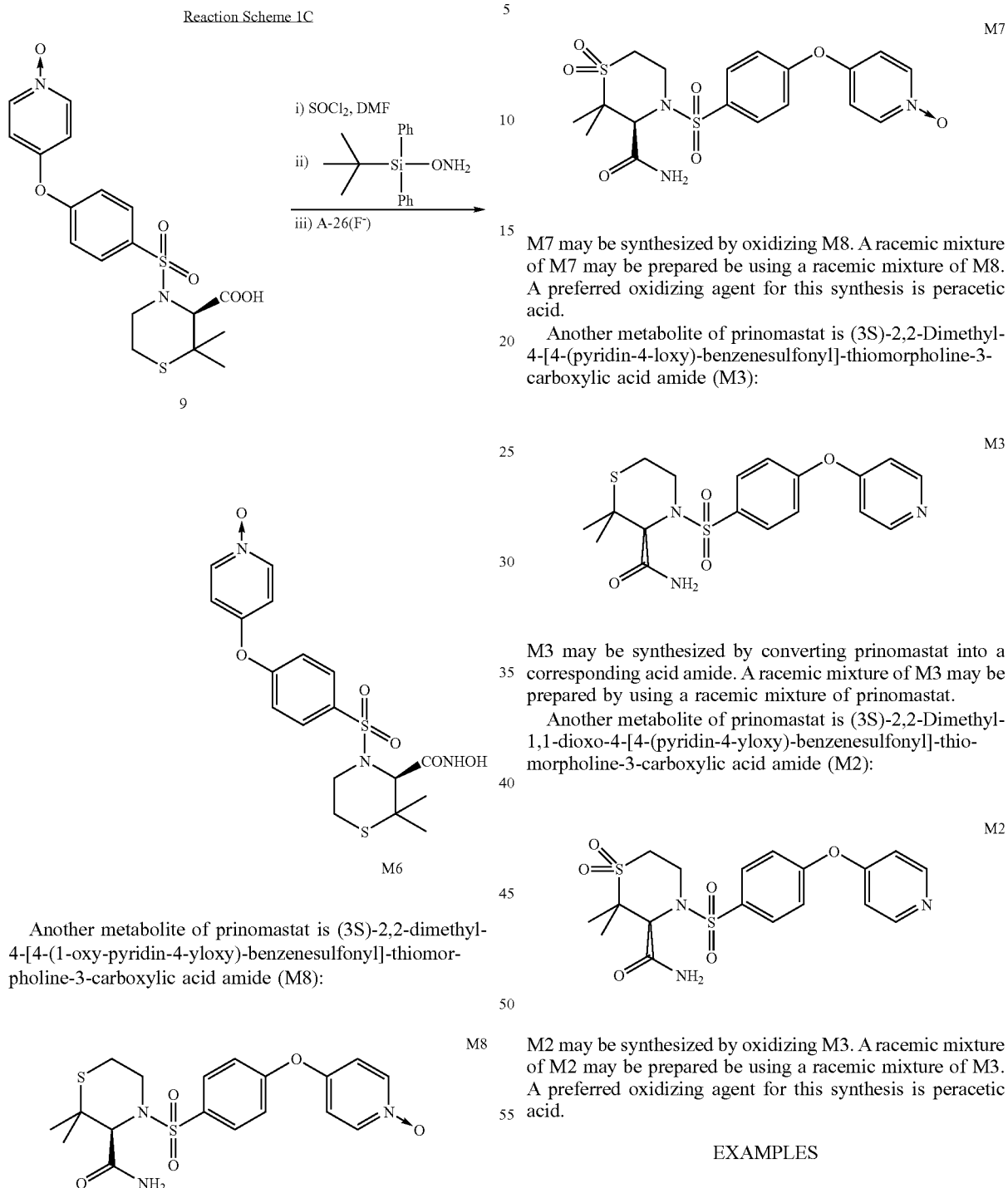

Another metabolite of prinomastat is (3S)-2,2-dimethyl-4-[4-(1-oxy-pyridin-4-yloxy)-benzenesulfonyl]-thiomorpholine-3-carboxylic acid amide (M8):

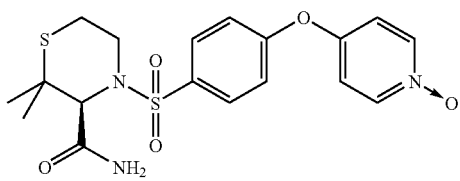

M8 may be synthesized by converting metabolite M6 into a corresponding acid amide. A racemic mixture of M8 may be prepared be using a racemic mixture of M6. M8 can also be prepared by either using ammonia in step (vii) of Reaction Scheme 1A or an N-protected amine in Reaction Scheme 1C wherein the amine is then deprotected to give M8.

A further metabolite of prinomastat is (3S)-2,2-Dimethyl-1,1-dioxo-4-[4-(1-oxy-pyridin-4-yloxy)-benzenesulfonyl]-thiomorpholine-3-carboxylic acid amide (M7):

M7 may be synthesized by oxidizing M8. A racemic mixture of M7 may be prepared be using a racemic mixture of M8. A preferred oxidizing agent for this synthesis is peracetic acid.

Another metabolite of prinomastat is (3S)-2,2-Dimethyl-4-[4-(pyridin-4-loxy)-benzenesulfonyl]-thiomorpholine-3-carboxylic acid amide (M3):

M3 may be synthesized by converting prinomastat into a corresponding acid amide. A racemic mixture of M3 may be prepared by using a racemic mixture of prinomastat.

Another metabolite of prinomastat is (3S)-2,2-Dimethyl-1,1-dioxo-4-[4-(pyridin-4-yloxy)-benzenesulfonyl]-thiomorpholine-3-carboxylic acid amide (M2):

M2 may be synthesized by oxidizing M3. A racemic mixture of M2 may be prepared be using a racemic mixture of M3. A preferred oxidizing agent for this synthesis is peracetic acid.

EXAMPLES

In the examples described below, unless otherwise indicated, all temperatures in the following description are in degrees Celsius (° C.) and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal® bottles and used as received. All solvents were purified using standard methods in the art, unless otherwise indicated.

The reactions set forth below were performed under a positive pressure of nitrogen, argon, or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography (TLC) was performed on glass-backed silica gel 60° F. 254 plates (Analtech (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat. Work-ups were typically done by doubling the reaction volume with the reaction solvent or extraction solvent and then washing with the indicated aqueous solutions using 25% by volume of the extraction volume (unless otherwise indicated). Product solutions were dried over anhydrous $Na_2SO_4$ prior to filtration, and evaporation of the solvents was under reduced pressure on a rotary evaporator and noted as solvents removed in vacuo. Flash column chromatography [Still et al., *A. J. Org. Chem.* 43:2923 (1978)] was conducted using Baker-grade flash silica gel (47–61 mm) and a silica gel:crude material ratio of about 20:1 to 50:1, unless otherwise stated. Hydrogenolysis was done at the pressure indicated or at ambient pressure.

$^1$H-NMR spectra was recorded on a Bruker instrument operating at 300 MHz, and $^{13}$C-NMR spectra was recorded operating at 75 MHz. NMR spectra are obtained as $CDCl_3$ solutions (reported in ppm), using chloroform as the reference standard (7.25 ppm and 77.00 ppm) or $CD_3OD$ (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra (IR) were recorded on a Perkin-Elmer FT-IR Spectrometer as neat oils, as KBr pellets, or as $CDCl_3$ solutions, and when reported are in wave numbers ($cm^{-1}$). The mass spectra were obtained using LC/MS or APCI. All melting points are uncorrected.

B. Pharmaceutical Compositions and Methods

The present invention is further directed to methods of inhibiting metalloproteinase activity, for example in mammalian tissue, by administering metabolites of prinomastat, such as a compound of the formula 11 or 22, or a pharmaceutically acceptable prodrug, salt or solvate thereof. The activity of the inventive compounds as inhibitors of metalloproteinase activity, such as the activity of MMPs (including stromelysins, collagenases, gelatinases, and/or matrilysin) and/or TNF-□ convertase, may be measured by any of the methods available to those skilled in the art, including in vivo and/or in vitro assays. Examples of suitable assays fro activity measurements include those described in *Anal. Biochem.*, 147, 437 (1995), *Anal. Biochem.*, 180, 110 (1989), *FEBS*, 96, 263 (1992) and European Patent Application No. 0 606 046.

Administration of a metabolite of prinomastat, such as a compound of the formula 11 or 22, or their pharmaceutically acceptable prodrugs, salts or solvates, may be performed according to any of the accepted modes of administration available to those skilled in the art. Illustrative examples of suitable modes of administration include oral, nasal, parenteral, topical, transdermal and rectal. Preferably, the mode of administration is oral.

The metabolites described herein, or their pharmaceutically acceptable prodrugs, salts or solvates, may be administered as a pharmaceutical composition in any suitable pharmaceutical form recognizable to the skilled artesian. Suitable pharmaceutical forms include: solid, semisolid, liquid or lyophilized formulations, such as tablets, powders, capsules, suppositories, suspensions, and aerosols. Preferably, the pharmaceutical form is a tablet or capsule for oral administration. The pharmaceutical composition may also include suitable excipients, diluents, vehicles and carriers as well as other pharmaceutically active agents, depending upon the intended use.

The inventive compounds of the formula 11 or 22, or their pharmaceutically acceptable prodrugs, salts or solvates, may be administered as a pharmaceutical composition in any suitable pharmaceutical form recognizable to the skilled artisan. Suitable pharmaceutical forms include: solid, semisolid, liquid or lyophilized formulations, such as tablets, powders, capsules, suppositories, suspensions and aerosols. Preferably, the pharmaceutical form is a tablet or capsule for oral administration. The pharmaceutical composition may also include suitable excipients, diluents, vehicles and carriers as well as other pharmaceutically active agents, depending upon the intended use.

Acceptable methods for preparing suitable pharmaceutical forms of the pharmaceutical compositions are known to those skilled in the art. For example, pharmaceutical preparations may be prepared following conventional techniques of the pharmaceutical chemist involving steps such as mixing, granulating and compressing when necessary for tablet forms, or mixing, filling, and dissolving the ingredients as appropriate, to give desired products for oral, parenteral, topical, intravaginal, intranasal, intrabronchial, intraocular, intraaural and/or rectal administration. Illustrative examples of such methods include those described in *Remington's Pharmaceutical Sciences*, $18^{th}$ edition (1990).

Solid or liquid pharmaceutically acceptable carriers, diluents, vehicles or excipients may be employed in the pharmaceutical compositions. Illustrative solid carriers include starch, lactose, calcium sulphate dihydrate, terra alba, sucrose, talc, gelatin, agar, pectin, acacia, magnesium stearate and stearic acid. Illustrative liquid carriers include syrup, peanut oil, olive oil, saline solution and water. The carrier or diluent may include a suitable prolonged-release material, such as glyceryl monostearate or glyceryl distearate, aloe or with a wax. When a liquid carrier is used, the preparation may be in the form of a syrup, elixir, emulsion, soft gelatin capsule, sterile injectable liquid (e.g. solution), or a non-aqueous or aqueous liquid suspension.

A dose of the pharmaceutical composition contains at least a therapeutically effective amount of the active compound (i.e., a metabolite of prinomastat, such as a compound of the formula 11 or 22, or their pharmaceutically acceptable prodrugs, salts or solvates) and preferably is made up of one or more pharmaceutical dosage units. An exemplary dosage unit for a mammalian host contains an amount of from 0.1 milligram up to 500 milligrams of active compound per kilogram body weight of the host, preferably 0.1 to 200 milligrams, more preferably 50 milligrams or less, and even more preferably about 10 milligrams or less, per kilogram of the host weight. The selected dose may be administered to a mammal, for example, a human patient in need of treatment mediated by inhibition of metalloproteinase activity, by any known method of administrating the dose including: topically, for example, as an ointment or cream; orally; rectally, for example, as a suppository; parenterally by injection; or continuously by intravaginal, intranasal, intrabronchial, intraaural or intraocular infusion.

The amount of the metabolites, salts, solvates and/or prodrugs to be administered will vary based upon a number of factors, including the specific metalloproteinase to be inhibited, the degree of inhibition desired, the characteristics of the mammalian tissue in which inhibition is desired, the metabolic stability and activity of the particular inventive compound employed, and the mode of administration. One skilled in the art may readily determine a suitable dosage according to methods known to the art. Preferably, the amount of inventive compound of the formula 11 or 22, or their pharmaceutically acceptable prodrugs, salts or solvates, administered is between 0.1 mg/kg body weight and 100 mg/kg body weight per day.

The following examples are given for the purpose of illustrating various embodiments and features of the invention.

Example 1A

Preparation and Purification of Metabolite M6

1. Acetylation of 4-Hydroxybenzensulfonic Acid Sodium Salt:

4-Hydroxybenzensulfonic acid sodium salt dihydrate (1400 g, 6.03 mol) was suspended in triethylamine (7 L) and acetic anhydride (1.7 L, 18.1 mol) was added over 1 hour. Exotherm to 70° C. was observed. When the temperature reached 70° C., a water bath was placed under the flask and used for cooling during the remainder of the acetic anhydride addition. The thick, gelatinous mixture was stirred at 20° C. for 15 hours. The solvent was removed by rotary evaporation under reduced pressure. The vacuum was controlled carefully to avoid bumping. Toluene (2 L) was added to the residue. Then, the mixture was concentrated by rotary evaporation. The toluene azeotrope was repeated giving a thick white suspension. The residue was suspended in ethyl acetate (8 L), and the mixture was refluxed for 1 hour. The mixture was cooled to 50° C., and the solid was collected by filtration, washed with ethyl acetate (2 L) and dried in a vacuum oven at 50° C. for 15 hours to give 1295 g (90% yield) of the acetate (See Cevasco, G. et al., *J. Org. Chem.* 61: 20, 6814–6817, (1996)).

2. 4-Acetoxy Benzenesulfonyl Chloride:

4-Acetoxybenzenesulfonic acid sodium salt (1890 g, 7.93 mol) was suspended in thionyl chloride (6 L). Dimethylformamide (DMF) (20 mL) was added and the mixture was heated to reflux (80° C.) over 1 hour and maintained at reflux for 1 hour. The mixture became less viscous and more yellow as the reaction progressed. The reaction progress can be checked by $^1$H NMR, if desired.

The mixture was cooled slightly and the solvent removed on a rotary evaporator. Toluene (4 L) was added to the residue and then removed by rotary evaporation. Dichloromethane (12 L) was added followed by Celite (320 g) and the resulting mixture was stirred for fifteen minutes and then filtered (32-cm funnel) to remove the insoluble inorganic salts. The filtrate was concentrated to about 3 L and hexane (4 L) was added, forming yellow crystals. Evaporation was continued until 4 L of solvent were removed. Hexane (3 L) was added and the solid was collected by filtration, washed with hexane (1 L), and dried under vacuum at 30° C. for 15 hours, giving 1585 g (85% yield) of 4-acetoxybenzenesulfonyl chloride as a yellow solid (See Cevasco, supra (1996)).

3. 4-(4-Acetoxy-benzenesulfonyl)-2,2-dimethyl-thiomorpholine-3(S)-carboxylic Acid tert-Butyl Ester:

A 22 L, 3-neck flask equipped with a mechanical stirrer, addition funnel, and thermometer was charged with 2,2-dimethyl-thiomorpholine-3(S)-carboxylic acid tert-butyl ester (896 g, 3.35 mol) and dichloromethane (9 L), giving a clear, colorless solution. The sulfonyl chloride (785 g, 3.35 mol) was added. Then, triethylamine (1.03 L, 7.36 mol) was added from the addition funnel over a span of 45 minutes. Exotherm to 28° C. and precipitate formation were observed. The mixture was stirred for 24 hours (sulfonyl chloride was still present by TLC analysis, 7:3 dichloromethane/hexanes). The mixture was poured into water (5 L) and stirred for 30 minutes. The phases were separated and the organic layer was washed with aqueous sodium bicarbonate (500 g in 5 L). The phases were separated. The organic layer was filtered through a pad of Celite (200 g), silica gel (900 g), and sodium sulfate (500 g) in a 24 cm Buchner funnel. The filtrate (slightly decolorized) was concentrated by rotary evaporation to approximately 2 L, and hexane (4 L) was added, forming a precipitate. Evaporation was continued until about 4 L of solvent were removed. Hexane (4 L) was added and the solid product was collected by filtration, washed with hexane (4 L) and dried in a vacuum oven at 25° C. for 48 hours, giving 1112 g (77% yield) of 4-(4-Acetoxy-benzenesulfonyl)-2,2-dimethyl-thiomorpholine-3(S)-carboxylic acid tert-butyl ester. This compound had the following properties: m.p. 136.6° C.; $[\alpha]_D^{25}=-8.5°$ (c 0.61, MeOH); IR (KBr): 2984, 2945, 1769, 1738, 1587, 1491, 1344, 1196, 1157 cm$^{-1}$; $^1$H NMR (300 MHz, CDCl$_3$): δ 7.75 (d, J=8.8 Hz, 2H, ArH), 7.21 (d, J=8.8 Hz, 2H, ArH), 4.33 (s, 1H, C$^\alpha$H), 4.06 (dd, J=12.1 and 2.6 Hz, 1H), 3.88 (dt, J=12.5 and 2.6 Hz, 1H), 3.12 (dt, J=13.2 and 4.0 Hz, 1H), 2.43 (br d, J=14 Hz, 1H), 2.30 (s, 3H, CH$_3$), 1.61 (s, 3H, CH$_3$), 1.33 (s, 3H, CH$_3$), 1.28 (s, 9H, Bu$^t$); $^{13}$C NMR (75 MHz, CDCl$_3$): δ 168.3 (C=O), 167.5 (C=O), 154.3, 137.8, 128.9 (×2), 122.4 (×2), 82.7, 63.9, 41.6, 40.6, 29.1, 28.3 (×3), 27.8, 25.0, 21.1; Anal. Calculated for C$_{19}$H$_{27}$NO$_6$S$_2$: C, 53.13; H, 6.34; N, 3.26; S, 14.93. Found: C, 53.26; H, 6.41; N, 3.30; S, 14.85.

4. 4-(4-Hydroxy-benzenesulfonyl)-2,2-dimethyl-thiomorpholine-3(S)-carboxylic Acid tert-Butyl Ester:

A suspension of 4-(4-Acetoxy-benzenesulfonyl)-2,2-dimethyl-thiomorpholine-3(S)-carboxylic acid tert-butyl ester (1 kg, 2.33 mol) and potassium carbonate (354 g, 2.56 mol) in methanol (5 L) and water (500 mL) was stirred at ambient temperature (internal temp=28° C.) for 3.5 hours. The reaction was determined to be complete by TLC (1:1 EtOAc/hexane). The solvent was removed under vacuum. The residue was diluted with water (5 L) and the pH adjusted to 2 with 12 M hydrochloric acid (~400 mL). The resulting solid was collected by filtration, washed with water, and dried in a vacuum oven at 60° C. to give 879 g of 4-(4hydroxy-benzenesulfonyl)-2,2-dimethyl-thiomorpholine-3(S)-carboxylic acid tert-butyl ester (97% yield). This compound had the following properties: m.p. 171.3° C.; $[\alpha]_D^{25}=-1.97°$ (c 0.61, MeOH); IR (KBr): 3376, 2978, 2936, 1734, 1601, 1587, 1369, 1325 cm$^{-1}$; $^1$H NMR (300 MHz, CDCl$_3$): δ 7.61 (d, J=8.8 Hz, 2H, ArH), 6.86 (d, J=8.8 Hz, 2H, ArH), 4.30 (s, 1H, C$^\alpha$H), 4.04 (m, 1H), 3.85 (dt, J=12.7 and 2.6 Hz, 1H), 3.11 (dt, J=13.6 and 4.1 Hz, 1H), 2.43 (br d, J=13.6 Hz, 1H), 1.60 (s, 3H, CH$_3$), 1.33 (s, 3H, CH$_3$), 1.31 (s, 9H, Bu$^t$); $^{13}$C NMR (75 MHz, CDCl$_3$): δ168.1 (C=O), 160.3, 131.8, 129.7 (×2), 116.2 (×2), 82.8, 63.9, 41.5, 40.6, 29.1, 28.3 (×3), 27.8, 25.0; Anal. Calculated for C$_{17}$H$_{25}$NO$_5$S$_2$+0.5% water (Karl Fisher analysis): C, 52.69; H, 6.50; N, 3.61; S, 16.55. Found: C, 52.73; H, 6.54; N, 3.64; S, 16.45.

5. 2,2-Dimethyl-4-[4-(1-oxy-pyridin-4-yloxy)-benzenesulfonyl]-thiomorpholine-3(S)-carboxalic Acid tert-Butyl Ester:

A 12 L, 3-neck flask equipped with a mechanical stirrer, thermocouple, condenser, and heating mantle was charged with 4-(4-hydroxy-benzenesulfonyl)-2,2-dimethyl-thiomorpholine-3(S)-carboxylic acid tert-butyl ester (1708 g, 4.41 mol), 4-nitropyridine N-oxide (1162 g, 8.29 mol), potassium carbonate (1231 g, 8.91 mol), and DMF (1.71 L). The mixture was heated to 110° C. over 3 hours and maintained at 110° C. for 3 hours, with monitoring by an HPLC system. After 6 hours total reaction time, the heat was turned off and the mixture cooled with stirring for 15 hours. Water (4 L) and dichloromethane (1.5 L) were added and the thick mass was transferred to a 50-L extractor. Additional water (6.3 L) was added and the mixture was extracted with dichloromethane (3×6.8 L). The combined organics were concentrated to an oil on the rotary evaporator. The residue was transferred to a 22-L flask and methyl tert-butyl ether (8.5 L) was added. After stirring for 1 hour, the resulting precipitate was collected by filtration, washed with methyl tert-butyl ether (MTBE) (2.5 L), and dried in a vacuum oven at 30° C., giving 1850 g (87% yield) of 2,2-dimethyl-4-[4-(1-oxy-pyridin-4-yloxy)benzenesulfonyl]-thiomorpholine-3(S)-carboxylic acid tert-butyl ester. This compound had the following properties: m.p. 182° C.; [α]$_D^{25}$=−27.9° (c 0.73, MeOH); IR (KBr): 3113, 2982, 2920, 1732, 1591, 1474, 1341, 1231, 1155 cm$^{-1}$; $^1$H NMR (300 MHz, CDCl$_3$): δ 8.19 (d, J=7.7 Hz, 2H, ArH), 7.80 (d, J=8.8 Hz, 2H, ArH), 7.14 (d, J=8.8 Hz, 2H, ArH), 6.90 (d, J=7.4 Hz, 2H, ArH), 4.36 (s, 1H, C$^α$H), 4.06 (m, 1H), 3.85 (dt, J=12.5 and 2.9 Hz, 1H), 3.14 (dt, J=12.9 and 4.05 Hz, 1H), 2.44 (br d, J=14.0 Hz, 1H), 1.63 (s, 3H, CH$_3$), 1.35 (s, 3H, CH$_3$), 1.32 (s, 9H, Bu$^t$); $^{13}$C NMR (75 MHz, CDCl$_3$): δ 167.6 (C=O), 158.4, 154.1, 141.0 (×2), 137.2, 130.1 (×2), 119.9 (×2), 116.3 (×2), 82.6, 64.0, 41.7, 40.7, 29.1, 28.3 (×3), 28.0, 25.0; MS(FAB) (m/z) calculated for C$_{22}$H$_{29}$N$_2$O$_6$S$_2$ (MH$^+$) 481, found 481 (MH+), 613 (MCs$^+$); Anal. Calculated for C$_{22}$H$_{28}$N$_2$O$_6$S$_2$: C, 54.98; H, 5.87; N, 5.83; S, 13.34. Found: C, 54.98; H, 5.87; N, 5.83; S, 13.24.

6. 2,2-Dimethyl-4-[4-(1-oxy-pyridin-4-yloxy)benzenesulfonyl]-thiomorpholine-3(S)-carboxylic Acid:

A 12 L, 3-neck flask equipped with a mechanical stirrer was charged with 2,2-dimethyl-4-[4-(1-oxy-pyridin-4-yloxy)benzenesulfonyl]-thiomorpholine-3(S)-carboxylic acid tert-butyl ester (1845 g, 3.84 mol), dichloromethane (3.7 L), trifluoroacetic acid (3.52 L), and anisole (440 mL, 4.07 mol). The mixture was stirred at 20° C. for 15 hours. The resulting solution was concentrated by rotary evaporation. Toluene (2 L) was added and evaporation continued and the residue was transferred into a 50-L extractor. Ethyl acetate (1.7 L) and water (3.4 L) were added, followed by solid potassium carbonate to adjust the pH to 3. Methyl Tertbutyl Ester, MTBE, (8.8 L) was added and the mixture was stirred for 15 hours. The precipitate was collected by filtration. The wet cake was transferred to the 50-L extractor and 2-propanol (3.7 L) was added. After stirring for 5 minutes, MTBE (22 L) was added. The mixture was stirred for 45 minutes and then filtered to collect the solid. The solid was washed with MTBE (6 L), pressed with a rubber dam for 6 hours and then dried in a vacuum oven at 40° C. for 9 hours, giving 1126 g (69% yield) of 2,2-dimethyl-4-[4-(1-oxy-pyridin-4-yloxy)benzenenesulfonyl]-thiomorpholine-3(S)-carboxylic acid. This acid had the following properties: $^1$H NMR (300 MHz, CDCl$_3$): δ 8.12 (d, J=7.7 Hz, 2H, ArH), 7.78 (d, J=8.5 Hz, 2H, ArH), 7.13 (d, J=8.8 Hz, 2H, ArH), 6.92 (d, J=7.7 Hz, 2H, ArH), 4.32 (s, 1H, C$^α$H), 4.03 (dt, J=11.8 and 3.3 Hz, 1H), 3.73 (dt, J=12.5 and 2.95 Hz, 1H), 3.10 (dt, J=13.1 and 3.7 Hz, 1H), 2.41 (br d, J=14.0 Hz, 1H), 1.60 (s, 3H, CH$_3$), 1.31 (s, 3H, CH$_3$); MS(FAB) (m/z) calculated for C$_{18}$H$_{21}$N$_2$O$_6$S$_2$ (MH$^+$) 425, found 425 (MH$^+$), 446 (MNa$^+$); Anal. Calculated for Cl$_{18}$H$_{20}$N$_2$O$_6$S$_2$: C, 51.00; H, 4.82; N, 6.50; S, 15.08. Found: C, 50.93; H, 4.75; N, 6.60; S, 15.11.

7. 3S-N-hydroxy-4-(4-((1-oxy-pyrid-4-yl)oxy)benzenesulfonyl)-2,2-dimethyl-tetrahydro-2H-1,4-thiazine-3-carboxamide (M6):

Dry DMF (10 drops) was added to a solution of the trifluoroacetate salt of 2,2-dimethyl-4-[4-(1-oxy-pyridin-4-yloxy)benzenesulfonyl]-thiomorpholine-3(S)-carboxylic acid (5 g, 0.009 mol) in thionyl chloride (25 mL), and the solution was stirred at room temperature for 5 hours. Thionyl chloride was removed under vacuum and the residue dissolved in dichloromethane was re-concentrated twice. The solid obtained was dried under high vacuum. The chemical shift of the α-proton is indicative of the formation of the 2,2-dimethyl-4-[4-(1-oxy-pyridin-4-yloxy)benzenesulfonyl]-thiomorpholine-3(S)-carboxylic acid chloride (acid chloride: δ 4.83; acid: δ 4.05).

The solid was dissolved in dichloromethane (30 mL) and slowly added to a solution of hydroxylamine in water (50%, 10 mL) and ethanol (20 mL) over 1 hour. The solution was further stirred at room temperature for 2 hours. HPLC of the solution indicated nearly 50% conversion. The solution was concentrated under vacuum to remove the volatile compounds. Water was azeotroped out with toluene. The residue was dried under vacuum to obtain a colorless solid. The solid was subjected to repeated silica gel column chromatography using methanol in dichloromethane (10–20%) containing acetic acid (1%) as the solvent to obtain nearly a gram of the material that contained acetic acid. Acetic acid was removed by salting out with triethylamine.

Triethylamine was difficult to remove from the product. Azeotroping with benzene reduced the triethylamine content, and pure material was obtained by precipitating with methanol-dichloromethane-ether. The solid was dried under high vacuum to obtain 3S-N-hydroxy-4-(4-((1-oxy-pyrid-4-yl)oxy)benzenesulfonyl)-2,2-dimethyl-tetrahydro-2H-1,4-thiazine-3-carboxamide (520 mg). Metabolite M6 was observed to have the following properties: m.p. 166–168° C.; [α]$_D^{25}$=38.3° (c 0.12, MeOH); IR (KBr): 1671, 1630, 1480, 1341, 1204, 1154 cm$^{-1}$; $^1$H NMR (300 MHz, CD$_3$OD): δ 8.32 (d, J=7.7 Hz, 2H, ArH), 7.91 (d, J=8.8 Hz, 2H, ArH), 7.37 (d, J=8.5 Hz, 2H, ArH), 7.28 (d, J=7.7 Hz, 2H, ArH), 4.09 (s, 1H, C$^α$H), 3.99–4.09 (m, 2H), 3.12 (m, 1H), 2.57 (br d, J=14.0 Hz, 1H), 1.62 (s, 3H, CH$_3$), 1.26 (s, 3H, CH$_3$); $^{13}$C NMR (75 MHz, CD$_3$OD): δ 165.4 (C=O), 158.5, 157.9, 141.2 (×2), 136.4, 130.0 (×2), 121.0 (×2), 116.1 (×2), 60.2, 42.2, 39.8, 28.1, 26.4, 24.6; $^1$H NMR (300 MHz, DMSO-d$_6$): δ 10.66 (br s, 1H), 8.91 (d, J=4.5 Hz, 1H), 8.19 (d, J=7.8 Hz, 2H), 7.74 (d, J=9.0 Hz, 2H), 7.29 (d, J=9.0 Hz, 2H), 7.16 (d, J=7.8 Hz, 2H), 4.00 (s, 1H), 3.99 (m, 1H), 3.82 (dt, J=3.2 and 12.6 Hz, 1H), 2.91 (dt, J=3.5 and 13.1 Hz, 1H), 2.55 (br d, J=13.8 Hz, 1H), 1.41 (s, 3H), 1.15 (s, 3H); $^{13}$C NMR (75 MHz, DMSO-d$_6$): δ 163.7, 158.2, 152.8, 140.3 (×2), 134.7, 129.3 (×2), 119.5 (×2), 116.8 (×2), 58.9, 41.3, 39.4 (obscured by DMSO signal in 1D 13C NMR spectrum but detected by HMBC), 28.4, 26.6, 2.0; HRFABMS (m/z): 440.0963 (MH$^+$); $C_{18}H_{22}N_3O_6S_2$ requires: 440.0950; Optical purity: 91% based on chiral HPLC assay.

Example 1B

Alternative Preparation of Metabolite M6

1. Preparation of O-(tert-butlyldiphenylsilyl)-hydroxylamine:

Under nitrogen, a 50 L extractor was charged with dichloromethane (20 L), triethylamine (7.1 L, 50.9 mol), and hydroxylamine hydrochloride (1769 g, 25.5 mol). The mixture was stirred for 45 minutes then tert-butylchlorodiphenylsilane (7 kg, 25.5 mol) was added in seven 1 kg portions over 40 minutes. Additional dichloromethane (10 L) was added, filling the vessel to capacity. The joints were stoppered and the mixture stirred at 20° C. for 5 days. The resulting thick white suspension was filtered to remove the precipitate (mostly triethylamine hydrochloride). The filtrate was concentrated to a thick paste by rotary evaporation on two separate evaporators. Ethyl acetate (4 L) was added to each portion and evaporation continued until 2 L of solvent were condensed. The suspension from each half was combined in the 50-L reactor, ethyl acetate (28 L) was added, and the mixture was stirred for 15 minutes. The mixture was filtered (removing the remaining triethylamine hydrochloride) and the solvent evaporated (again using two rotary evaporators). When most of the solvent was removed, hexane (4 L) was added to each portion and evaporation continued until 2 L of solvent were condensed. The two halves were combined in the 50-L reactor, hexane (20 L) was added, and the mixture was stirred for 15 minutes. The resulting white solid was collected by filtration, washed with hexanes, and dried in a vacuum oven at 40° C., giving 4780 g (69% yield) of O-(tert-butyldiphenylsilyl)-hydroxylamine.

2. Preparation of 3S-N-hydroxy-4-(4-((1-oxy-pyrid-4-yl) oxy)benzenesulfonyl)-2,2-dimethyl-tetrahydro-2H-1,4-thiazine-3-carboxamide (M6):

A 12 L, 3-neck flask equipped with a mechanical stirrer, thermometer, and nitrogen inlet was charged with 2,2-dimethyl-4-[4-(1-oxy-pyridin-4-yloxy)benzenesulfonyl]-thiomorpholine-3(S)-carboxylic acid (1121 g, 2.64 mol), thionyl chloride (2.24 L), and DMF (2 mL). An exotherm to 37° C. was observed. The mixture was stirred at ambient temperature for 6 hours, with occasional monitoring by $^1$H NMR. The resulting yellow suspension was concentrated to a thick oil by rotary evaporation. Dichloromethane (2 L) was added and evaporated, giving a yellow foam. Dichloromethane (2 L) was added again and evaporated. The resulting yellow foam was dried on the rotary evaporator for 15 hours.

The acid chloride was dissolved in dichloromethane (4.4 L) and the solution charged to a 50-L extractor. O-tert-(Butyldiphenylsilyl)-hydroxylamine (2254 g, 8.32 mol, 3.1 eq) was dissolved in dichloromethane (6.7 L) and the solution was added to the acid chloride solution. Exotherm to 33° C. was observed. The mixture was stirred at ambient temperature for 4 hours, with occasional monitoring by HPLC. The reaction was quenched by careful addition of aqueous sodium bicarbonate (1.34 kg in 11.2 L water). After stirring for 5 minutes, the phases were split. The organic layer was washed with water (6.7 L) and then concentrated by rotary evaporation to a thick orange oil.

The orange oil (silyl-protected metabolite M6) was dissolved in methanol (22.4 L) and Amberlite A-26™ fluoride resin (67.3 g) was added. The mixture was maintained at 20° C. for 60 hours. Because HPLC analysis showed starting material, additional fluoride resin (20 g) was added. HPLC after 8 hours showed little change, so additional fluoride resin (40 g) was added and the mixture was stirred for 15 hours. At this point, HPLC analysis indicated that the reaction was complete. The resin was removed by filtration and the filtrate was concentrated to about 3 L by rotary evaporation (crystallization occurred during evaporation). The mixture was diluted with MTBE (12 L) and stirred for 15 minutes. The solid was collected by filtration and washed with MTBE (2 L). The wet cake was stirred with ethanol (3.8 L) for 20 minutes. The solid was collected by filtration, washed with MTBE (2 L), and dried in a vacuum oven at 30° C. for 24 hours, giving 790 g (68% yield) of metabolite M6, as a methanol solvate.

Purification of Metabolite M6:

A 50-L cylindrical reactor equipped with a mechanical stirrer, thermometer, heating mantles, cooling coil, and condenser was charged with water (27 L). The water was heated to 100° C. and metabolite M6 (680 g) was added. The heating mantles were removed and the mixture was stirred for 5 minutes, giving a clear solution (a few large particles remained insoluble). Tap water (~10° C.) was run through the cooling coil, cooling the mixture to 50° C. within 5 minutes. Crystallization commenced at 65° C. The warm mixture was transferred to a 50-L extractor and cooled with stirring for 18 hours.

After rinsing well with water, the 50-L cylindrical reactor was charged with water (27 L). The water was heated to 100° C. and metabolite M6 (680 g) was added. The heating mantles were removed and after 5 minutes, tap water was run through the cooling coil. The temperature dropped to 50° C. within 5 minutes. The mixture was cooled with stirring for 15 hours. The mixture in the 50-L cylindrical reactor was filtered to collect the resulting crystals. The solid was washed with water (6 L) then transferred wet into the 50-L extractor containing the other half of the material. The mixture in the 50-L extractor was stirred for 15 minutes. The solid was collected by filtration, washed with water (6 L), and dried in a vacuum oven at 40° C. for 60 hours, giving 1192.8 g (88% yield) of metabolite M6 as a hydrate.

This method may also be used to purify M7, M8, M2 and M3.

Example 1C

Structural Characteristics of Metabolite M6 Synthetic Standard

The authentic standard metabolite M6 is the pyridine N-oxide analogue of prinomastat, and its product ion mass spectrum showed fragment ions at m/z 129, 186, 187, and 252.

The $^1$H and $^{13}$C chemical shifts of metabolite M6 authentic standard were assigned by comparative analysis with prinomastat and confirmed by $^1$H-$^{13}$C correlation experiments (HMQC and HMBC). The chemical shifts of the protons adjacent to the pyridine N-oxide nitrogen (δ 8.19) are upfield-shifted from those of the parent drug prinomastat (δ 8.51), as expected from established values for pyridine N-oxide and pyridine (see Pretsch et al., *Spectral Data for the Determination of Organic Compounds*, 2$^{nd}$ Ed., Springer-Verlag (1989)). When compared to the parent drug, only the pyridine N-oxide moiety of metabolite M6 gives rise to significant $^1$H and $^{13}$C chemical shift differences. All other $^1$H and $^{13}$C chemical shifts were essentially unchanged from those of prinomastat. The chemical shifts of prinomastat and metabolite M6 are shown by FIG. 1.

Example 1D

Analysis of Authentic Standard Metabolite M6

1. Human Studies:

Five healthy male volunteers received a 100 mg oral dose of prinomastat tablets in a phase I, double-blind, ascending single dose study. Blood samples were drawn at pre-selected time points, and the plasma was separated by centrifugation and stored at −20° C.

2. Sample Preparation for Liquid Chromatography Mass Spectroscopy (LC-MS):

The human plasma samples at 1.5, 4, 8 and 12 hours pooled from five male volunteers were selected for the analysis of metabolites by liquid chromatography tandem mass spectroscopy (LC-MS/MS). Samples were treated with three volumes of an AcN:MeOH mixture (2:1) to precipitate plasma proteins. Following centrifugation, protein pellets were separated and washed twice with two volumes of the same AcN:MeOH mixture. The combined supernatant was evaporated to dryness under vacuum using a SpeedVac™ (Savant Instrument, Holbrook, N.Y.), and the dried residue was reconstituted in 0.1% formic acid-acetonitrile (90:10), and analyzed by LC-MS/MS.

3. Standard Mixtures for LC-MS:

Standard solutions of prinomastat and metabolite M6 were prepared in methanol at 1 mg/mL concentrations. An aliquot (10 μL) of each was added to a 1 mL solution containing 90% formic acid (0.1%) and 10% acetonitrile. Thus, the final concentration of each compound was 10 μg/mL.

4. LC-MS/MS Analysis:

Two LC-MS/MS systems were used to analyze the plasma samples. The first system was operated at the Mass Spectrometry facility, of the Scripps Research Institute, and included: (a) an HPLC system (HP1090); (b) a narrow-bore column (Phenomenex Prodigy ODS2 2.0×150 mm); and (c) a triple quadrupole mass spectrometer (PE Sciex API III$^+$) using an electrospray interface. The mobile phase contained A=0.1% formic acid and B=AcN. Gradient elution was programmed linearly from 10% to 35% B over 25 min (1% per min.) at a flow rate of 200 μL/min. Mass spectrometer conditions were set as follows: ionspray voltage at 4,600 V, orifice potential at 80 V, nebulizing gas (high purity air) pressure at 40 psi, collision energy at 40 eV, and collision gas thickness at 160 units. To obtain molecular ion information, the mass spectrometer was operated in MS scan mode (m/z 200–700); to obtain structural information, the instrument was operated in MS/MS (daughter ion) scan mode. The scan rate was set at approximately 500 amu/sec.

The second LC-MS/MS analysis was conducted using a system including: (a) an HPLC system (Waters Alliance 2690); (b) a narrow-bore column (Waters Symmetry C$_{18}$, 2.1×150 mm); (c) UV detector (Waters 486 Tunable wavelength) set at 246 nm; and (d) a triple quadrupole mass spectrometer (Micromass Quattro 111) using an electrospray Crossflow™ ion source. The mobile phase contained A=0.1% formic acid and B=AcN. Gradient elution was programmed linearly from 10% to 40% B over 23 min (1.3% per min.) at a flow rate of 200 μL/min. Mass spectrometer conditions were set as follows: capillary voltage at 3.18 kV, HV lens at 0.8 kV, cone voltage at 45 V; source temperature at 140° C., collision energy at 30 eV, and collision gas cell pressure at $1.3 \times 10^{-3}$ mBar. To obtain molecular ion information, the mass spectrometer was operated in MS scan mode (m/z 200–700). To obtain structural information, the instrument was operated in MS/MS (daughter ion) scan mode. The scan rate was set at approximately 500 amu/sec.

The relative peak heights of prinomastat and its metabolites in the LC-MS reconstructed ion chromatograms (RIC) were used to estimate the relative abundance of each component, which was expressed as percent of total prinomastat related compounds.

Example 2

Preparation of (3S)-2,2-Dimethyl-1,1-dioxo-4-[4-(pyridin-4-yloxy)-benzenesulfonyl]-thiomorpholine-3-carboxylic Acid Amide (M2)

A suspension of 465 mg of (3S)-2,2-Dimethyl-4-[4-(pyridin-4yloxy)-benzenesulfonyl]-thiomorpholine-3-carboxylic acid amide (M3; 114 mmol), in 10 mL of dichloromethane was treated with peracetic acid (2.00 mL, 9.51 mmol, 8.33 eq.). The reaction was stirred at ambient temperature for 25 hours. The reaction was concentrated to give a white foam. The crude was purified by C-18 HPLC with acetonitrile and 0.5 M aqueous ammonium acetate buffer as an eluent in eight injections. The clean product fractions were combined and the organic solvent removed in vacuo. Fine white crystals fell out of the resulting aqueous solution. The crystals were collected by filtration, washed with water and then dried in vacuo. This gave 204 mg of metabolite M2 (41%) as fine white crystals.

Example 3

Preparation of (3S)-2,2-Dimethyl-1,1-dioxo-4-[4-(1-oxy-pyridin-4-yloxy)benzenesulfonyl]-thiomorpholine-3-carboxylic Acid Amide (M7)

A suspension of 435 mg of (3S)-2,2-Dimethyl-4-[4-(1-oxy-pyridin-4-yloxy)benzenesulfonyl]-thiomorpholine-3-carboxylic acid amide (M8; 1.03 mmol) in 5 mL of dichloromethane was treated with peracetic acid (2.00 mL, 9.51 mmol, 9.23 eq.). The reaction was stirred at ambient temperature for 29 hours. The reaction was concentrated. The crude product was purified by C-18 HPLC with acetonitrile and water with 0.1% trifluoroacetic acid as eluent in eight injections. The clean product fractions were combined and all solvents removed in vacuo. The residue was taken up in methanol and then filtered through a cotton plug and concentrated to give metabolite M7 as a white foam (157 mg M7 (34%) containing ~1% (w/w) methanol).

Example 4

Spectroscopic Identification and Structural Characterization of Prinomastat Metabolites Prinomastat, two of its sulfoxide diastereomers (DS1 and DS2), and all metabolites of prinomastat were synthesized and LC-MS analysis of samples (HPLC-grade acetonitrile and methanol, monobasic ammonium phosphate and formic acid) were obtained. Reagents used for LC-NMR analysis included acetonitrile, obtained from Aldrich (Riedel-de-Haen; NMR Chromasolv (LC-NMR grade)) and deuterium oxide (99.9% D; Cambridge Isotopes). Solid phase extraction cartridges (Sep-Pak Vac C18, 2 cc, 2 g) were obtained from Waters Corporation (Milford, Mass.).

A. Spectroscopic Tests:

1. Human Studies:

Five healthy male volunteers received a 100 mg oral dose of prinomastat tablets in a phase I, double-blind, ascending single dose study. Blood samples were drawn at pre-selected time points. Plasma was separated by centrifugation, stored at −20° C., and selected samples were used for analysis.

In a separate study, a single subject received a 25 mg dose of prinomastat every 12 hours for 3 days. Urine samples collected on day 3 (0–4 hr postdose, 4–8 hr postdose, and 8–12 hr postdose, 2×~20 mL each) were stored at −20° C. and solid phase extractions were performed.

2. Sample Preparation for LC-MS:

Human plasma pooled from five male volunteers was analyzed for metabolites at 1.5 hr, 4, 8 and 12 hours. Samples were treated with three volumes of an acetonitrile:methanol mixture (2:1) to precipitate plasma proteins. Following centrifugation, protein pellets were separated and washed twice with two volumes of the same acetonitrile/methanol mixture. The combined supernatant was evaporated to dryness under vacuum using a SpeedVac™ (Savant Instrument, Holbrook, N.Y.), and the dried residue was reconstituted in 0.1% formic acid-acetonitrile (90:10), and analyzed by LC-MS/MS.

3. Standard Mixtures for LC-MS:

Standard solutions of prinomastat and metabolite M6 were prepared in methanol at 1 mg/mL concentrations. An aliquot (10/µL) of each was added to a 1 mL solution containing 90% formic acid (0.1%) and 10% acetonitrile. Thus, the final concentration of each compound was 10 µg/mL.

4. LC-MS/MS Analysis:

Two LC-MS/MS systems were used to analyze the plasma samples. The first system included: (a) an HPLC system (HP1090); (b) a narrow-bore column (Phenomenex Prodigy ODS2 2.0×150 mm); and (c) a triple quadrupole mass spectrometer (PE Sciex API III$^+$) using an electrospray interface. The mobile phase contained A=0.1% formic acid and B-acetonitrile. Gradient elution was programmed linearly from 10% to 35% B over 25 min (1% per min) at a flow rate of 200 µL/min. Mass spectrometer conditions were set as follows: ionspray voltage at 4,600 V, orifice potential at 80 V, nebulizing gas (high purity air) pressure at 40 psi, collision energy at 40 eV, and collision gas thickness at 160 units. To obtain molecular ion information, the mass spectrometer was operated in MS scan mode (m/z 200–700); to obtain structural information, the instrument was operated in MS/MS (daughter) scan mode. The scan rate was set at approximately 500 amu/sec.

The second LC-MS/MS system included: (a) an HPLC system (Waters Alliance 2690); (b) a narrow-bore column (Waters Symmetry $C_{18}$, 2.1×150 mm); (c) UV detector (Waters 486 Tunable wavelength) set at 246 nm; and (d) a triple quadrupole mass spectrometer (Micromass Quattro II) using an electrospray Crossflow™ ion source. The mobile phase contained A=0.1% formic acid and B-Acetonitrile. Gradient elution was programmed linearly from 10% to 40% B over 23 minutes (1.3% per min.) at a flow rate of 200 µL/min. Mass spectrometer conditions were set as follows: capillary voltage at 3.18 kV, HV lens at 0.8 kV, cone voltage at 45 V, source temperature at 140° C., collision energy at 30 eV, and collision gas cell pressure at $1.3 \times 10^{-3}$ mBar. To obtain molecular ion information, the mass spectrometer was operated in MS scan mode (m/z 200–700). To obtain structural information, the instrument was operated in MS/MS (daughter ion) scan mode. The scan rate was set at approximately 500 amu/sec.

5. Sample Preparation for NMR:

Metabolites M7 and M2 were partially purified from 60 mL of human urine. Solid phase extraction (SPE) was used as the primary method of metabolite enrichment, and further purification was achieved by HPLC. The procedure used for M7 purification was as follows. The SPE column (Sep-Pak Vac C18, 12 cc, 2 g, Waters Corp.) was activated by rinsing with 40 mL of methanol followed by 40 mL of deionized water; the column was not allowed to dry between any of the elution steps. The sample (20 mL of human urine) was applied to the top of the column and drawn through the packing tad with vacuum at 0.025 bar. A slow flow rate was maintained. The column was washed with 20 ml of 0.1% aqueous formic acid followed by 50 mL of water and 50 mL of 10% methanol in water. Thereafter, the analyte was eluted into collection tubes with 50 mL of 30% methanol. An additional 20 mL of 40% methanol was passed through the column to wash off retained components. This process was repeated with another 2×20 mL urine. The SPE fractions were then concentrated to dryness on a Speed-Vac™ (Savant Instruments, Forma Scientific, Inc., Marietta, Ohio) and reconstituted with water to a final volume of approximately 1 mL. Each of the fractions was analyzed for the presence of M7 by LC/MS (as described below). The fractions containing M7 were pooled and concentrated on the Speed-Vac™ to a volume of approximately 1 mL. MS analysis indicated that these fractions also contained M2. Half of the M7-enriched sample was reserved for LC-NMR and LC-NMR-MS analysis. The remaining sample was further purified using HPLC, with the mass spectrometer to guide the purification process, in preparation for analysis on the NMR cryogenic probe.

The SPE fractions were analyzed by LC-MS for the presence of M7 and M2 as follows. The system included an HPLC system (Agilent HP1100) and a single quadrupole mass spectrometer (Micromass Platform LC) using an electrospray ion source. A reversed-phase HPLC column was used (Waters Symmetry C18, 4.6×150 mm). The mobile phase contained A=0.1% TFA/$H_2O$ and B=0.1% TFA/acetonitrile. Gradient elution was programmed linearly from 10% to 50% B over 20 min at a flow rate of 1.2 mL/min. The split ratio between LC and MS was 20:1. Mass spectrometer conditions were set as follows: capillary voltage at 3.51 kV, HV lens at 1.0 kV, cone voltage at 45 V, and source temperature at 120° C. The scan range was from 100 to 600 amu with scan time of 1.2 sec.

6. LC-NMR Analysis:

The metabolite-enriched fraction obtained by SPE of human clinical urine samples was analyzed by LC-NMR on a Bruker Avance DRX 500 MHz spectrometer. The system was configured with a 4 mm $^1H/^{13}C$ inverse geometry LC (LC SEI) probe equipped with X,Y,Z-gradients, an HP1100 analytical HPLC with binary pump and variable wavelength detector, and a Bruker 12-loop peak-sampling unit (BPSU-12). The LC-NMR software interface was HyStar NT Version 1.2. Chromatography was performed on a reversed phase column (Waters C18, 4.6×150 mm) using a gradient elution method at a flow rate of 1.2 mL/min. Mobile phase A contained 0.1% TFA in deuterium oxide (99.9% D), while mobile phase B contained 0.1% TFA in acetonitrile. The solvent gradient was increased linearly from 10% B to 65% B over 25 minutes. The UV absorbance was monitored at 246 nm LC-NMR was performed in stop-flow mode. The metabolite-enriched SPE fraction (20μ) was injected onto the LC column; M7 eluted with a retention time (Rt) of 7.42 minutes. In order to estimate the amount of M7 on column, known concentrations of metabolite M6 synthetic standard were analyzed by HPLC until a matching UV absorbance was found. The M7 peak was estimated to contain about 10 μg of material. Solvent suppression was performed using either double pre-saturation of the residual solvent resonances or WET solvent (see Smallcombe, S. H., et al., *J. Magn. Reson. Series A*, 117, 295303, 1995) suppression with $^{13}C$ decoupling. Spectra were acquired using 32K complex data points and a spectral width of 10 KHz. Temperature control was maintained at 27° C. Data was acquired with overnight acquisitions (~20 K transients) for the M7 clinical isolate sample.

In addition, control LC-NMR spectra were acquired on synthetic standards of prinomastat (10 μL of a 15 mg/mL dimethyl sulfoxide (DMSO) solution); M6 (10 μL of a 5 mg/mL DMSO solution); DS1 (10 μL of a 15 mg/mL DMSO solution); DS2 (10 μL of a 15 mg/mL DMSO solution); M2 (5 μL of a 30 mg/mL solution), and M7 (20 μL of a 20 mg/mL solution). Typically, data was acquired for approximately 1 hour (1–2 K transients) for these synthetic standards.

Finally, LC-NMR was performed on a crude reaction mixture obtained from the m-chloroperoxybenzoic acid (MCPBA) oxidation of M6. The mixture of reaction products was dissolved in $D_2O$: acetonitrile (5:1) to a concentration of 5 μg/μL and an aliquot (11 μL) was chromatographed using the method described above for M7. Stop-flow LC-NMR was performed on peaks eluting with retention times of 7.4, 8.2, and 9.03 minutes. NMR data was collected as described above using double pre-saturation and no more than 256 transients per FID.

7. LC-NMR-MS Analysis:

LC-NMR-MS system consisted of a DRX500 spectrometer interfaced to an HP1100 analytical HPLC with binary pump and diode array detector, and a 36-loop peak-sampling unit (BPSU-36). An Esquire 3000 ESI ion trap mass spectrometer completed the LC-NMR-MS system. NMR data acquisition parameters described above under LC-NMR Analysis were used to collect the data on M7 and M2, with the following exceptions. 1D data acquisition was performed with WET solvent suppression, with 2151 transients for M2 (Rt 7.01 min) and 5632 transients for M7 (Rt 7.42 min).

8. NMR Analysis on a Cryogenic Probe:

The M7-enriched sample obtained by SPE and mass spectrometry-guided was analyzed on a Broker Avance DRX 500 MHz spectrometer equipped with a 3 mm, $^1H/^{13}C$, Z-Gradient, cryogenic probe. M7 (~10 μg) was dissolved in $D_2O$ (150 μL). A 1D $_1HNMR$ spectrum was acquired in 32 scans with pre-saturation on the residual water resonance. COSY data was collected using gradient pulses for coherence selection and a pre-saturation pulse applied to the residual water. The data was acquired with 4 scans per increment and 256 complex data points in $t_1$ and 2K complex data points in $t_2$ for a total experiment time of 30 minutes. An HMQC data set was acquired using gradient pulses for coherence selection. The 2D spectrum was acquired with 128 scans per increment, 128 real data points in $t_1$ and 2K complex data point in $t_2$ for a total experiment time of approximately 7 hours. Finally, an HMBC data set was acquired using gradient pulses for coherence selection. The 2D spectrum was acquired with 1000 scans per increment, 128 complex data points in $t_1$ and 2K complex data points in $t_2$ for a total experiment time of approximately 56 hrs.

B. Results of Spectroscopic Tests:

1. LC-MS/MS:

The metabolic composition of human plasma following single oral dose administration of prinomastat is summarized in FIG. 1. The parent drug was the major circulating compound at early time points, while the major circulating metabolite, M6, represented as much as 50% of the total drug-related substance at later time points. M6 was identified by LC-MS/MS, as the pyridine N-oxide of prinomastat. The MS/MS data served as the basis for the identification of two additional N-oxide metabolites in human plasma, M7 and M8. Metabolite M8 was readily identified as the corresponding amide of M6 by LC-MS/MS analysis. The structure of M7 has also been confirmed by independent synthesis, as discussed above. However, the structure of M7 could not be determined by LC-MS alone.

Metabolite M7 appeared to be an oxidation product of M6, with m/z 456 ($MH^+$). The daughter ion spectrum of M7 yielded fragment ions at m/z 186, 187 and 250, consistent with the pyridine N-oxide, but lacked the tetrahydrothiazine (THTZ) fragment ion at m/z 129 (See FIG. 2B). The increased mass and apparent modification to the THTZ moiety suggested that M7 might be a sulfoxide of M6. However, the MS/MS spectra were noticeably different from those of DS1 and DS2, the sulfoxide diastereomers of prinomastat.

2. LC-NMR:

The spectrographic determination of M7's structure depended upon more detailed information available from NMR spectroscopy. LC-MS analysis of human clinical urine samples confirmed the presence of M7 in urine and indicated that the urine samples could serve as a source of M7 for NMR analysis. Thus, NMR studies were carried out on metabolite-enriched fractions obtained from solid phase extractions (SPE) of the human urine samples. Stop-flow LC-NMR spectra were compared with those of prinomastat and metabolite M6 synthetic standard, confirming that M7 was an N-oxide.

The collective LC-NMR data indicated that the aliphatic carbons of the THTZ ring were not oxidized. The gem-dimethyl signals, the THTZ methine proton and three of the four methylene protons of the THTZ ring were clearly present in the spectrum, and the coupling constants for the three observable methylene protons indicated that the fourth methylene proton must be present but obscured by the residual water resonance. The downfield shift of the THTZ aliphatic protons suggested that the site of oxidation was a heteroatom in the THTZ ring.

The LC-MS/MS data had suggested that M7 was not a sulfoxide. Moreover, the Δδ between the structurally diagnostic gem dimethyl resonances was much greater for M7 (86 Hz) than for either DS1 (35 Hz) or DS2 (23 Hz), the sulfoxides of prinomastat.

The reaction products were screened by LC-NMR, which allowed the chemical shifts of the gem-dimethyl protons to be rapidly determined. While the Δδ values for the two sulfoxide reaction products of M6 (40 Hz and 20 Hz) were consistent with those of DS1 and DS2, they were a poor fit for those of M7. Thus, LC-NMR provided a rapid screen of crude reaction products that allowed the N-oxide sulfoxide structures to he eliminated from consideration.

3. LC-NMR-MS:

Persistent differences between LC-NMR and LC-MS HPLC retention times were observed for several compounds in the metabolite-enriched fraction, including M7. Thus, the sample was analyzed by LC-NMR-MS, which allowed the NMR and MS data to be collected simultaneously during the same chromatographic run and provided absolute confirmation that the NMR and MS data were associated with the same compound. In addition, because LC-NMR-MS was performed with deuterated solvents, supplementary structural information was obtained by virtue of deuterium exchange. M7 gave a molecular ion at m/z 459 (M+$^2$H)$^+$, versus m/z 456 in protonated solvents, indicating the presence of two exchangeable protons. Finally, while LC-NMR had been performed in direct stop-flow mode, with compound transferred directly to the NMR after chromatography, LC-NMR-MS was performed with loop storage of the compound prior to transfer to the NMR probe. This effectively purified the sample by removing some of the leading and tailing components of the peak on the column and exemplified one of the benefits of loop storage.

4. High Resolution NMR Using a Cryogenic Probe:

Although the application of hyphenated techniques provided sufficient data to derive a structure for M7, proof of structure was obtained by high resolution 2D NMR. The metabolite-enriched SPE fraction was further purified for this purpose using HPLC with mass spectrometry-guided fractionation. The resulting M7 sample was analyzed using a cryogenic probe, as the available material (~10 μg) was well below the limits required for analysis on a conventional NMR probe. $^1$H-NMR spectra collected under these conditions indicated that the M7-enriched sample was not pure. However, by using the 1D LC-NMR spectrum as a reference, it was possible to identify those proton resonances associated with M7 and to ultimately assign the $^{13}$C resonances detected in the 2D cryogenic probe data. In the HMQC, the methylene protons adjacent to the THTZ sulfur (δ 3.23, 3.68) were correlated to a $^{13}$C resonance at δ 45.5. In the HMBC, the THTZ methine (δ 4.72) and gem-dimethyl (δ 1.41, 1.60) protons were correlated to a quaternary $^{13}$C resonance at δ 59.7. Thus, the $^{13}$C chemical shifts of the carbons flanking the THTZ sulfur were downfield-shifted by 20 ppm compared to those of prinomastat, clearly identifying sulfur as the site of oxidation. Having already shown that M7 was not a sulfoxide, the metabolite was shown to be a sulfone. The differences in mass spectra data are reconciled by the fact that M7 is an amide, as opposed to the hydroxamic acid. This structure allows for the two exchangeable protons required by the LC-MS deuterium exchange and accommodates the oxidation of the sulfur to the sulfone. In order to confirm this structure, the synthetic standard of metabolite M8 was oxidized with peracetic acid. The LC-NMR spectrum of the sulfone oxidation product was identical to that of M7.

5. LC-NMR-MS Analysis of Metabolite M2:

LC-NMR-MS was also performed on M2, an earlier eluting metabolite present in the metabolite-enriched SPE fraction obtained from the clinical urine samples. The parent ion was observed at m/z 443 (M+$^2$H)$^+$ in the mass spectrometer. In the NMR, M2 gave the same gem-dimethyl chemical shift pattern (Δδ=92 Hz) observed for M7 (Δδ=86 Hz), but showed an intact (unoxidized) pyridine ring. Having previously established that the chemical shifts of the gem-dimethyl signals were sensitive to changes in the structure of the THTZ ring, the close match between the chemical shifts of the M2 and M7 methyl signals showed that the metabolites were closely related, with M7 representing the pyridine N-oxide of M2. Using a similar strategy to that adopted for M7, peracetic acid oxidation was performed on M3, the corresponding amide of prinomastat. The sulfone reaction product (See FIG. 4C) gave an identical LC-NMR spectrum to that of M2 present in the clinical urine isolate.

As shown in Table 1, M6 is a potent inhibitor of MMP's.

TABLE 1

| Compound | K$_i$ value hCOL3 | K$_i$ value hGELA | K$_i$ value hCOL1 | K$_i$ value hMATR | K$_i$ value hSLN |
|---|---|---|---|---|---|
| M6 | 4 nm | 6.6 nm | 396 nm | 1140 nm | 5.1 nm |

The foregoing description has been provided to illustrate the invention and its preferred embodiments. The invention is intended not to be limited by the foregoing description, but to be defined by the appended claims.

What is claimed is:

1. A process for synthesizing a compound of formula 11, N-hydroxy-4-(4-((1-oxy-pyrid-4-yl)oxy)benzenesulfonyl)-2,2-dimethyl-tetrahydro-2H-1,4-thiazine-3-carboxamide, comprising the steps of:

(i) protecting a compound of formula 1

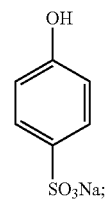

with a protecting group, P$_1$, to form a compound of formula 2

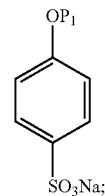

(ii) activating the compound of formula 2 with an activating agent, A$_1$, to form a compound of formula 3

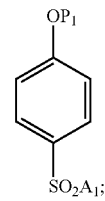

(iii) coupling the compound of formula 3 with a compound of formula 4 having an ester, E₁

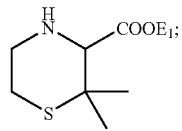

to form a compound of formula 5

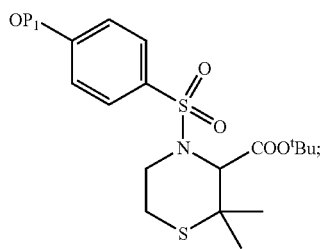

(v) removing the protecting group, P₁, from the compound of formula 5 to form a compound of formula 6

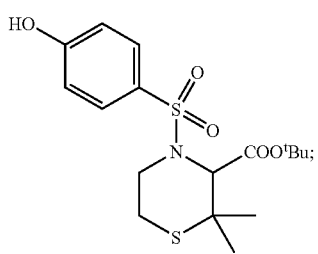

(vi) coupling the compound of formula 6 with p-nitro pyridine N-oxide, a compound of formula 7

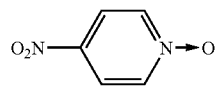

to form a compound of formula 8

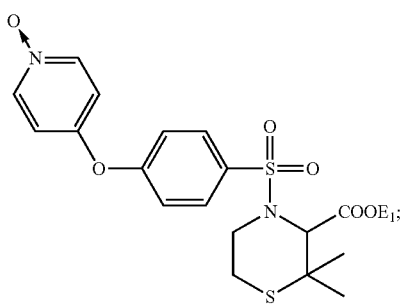

(vii) removing the ester, E₁, from the compound of formula 8 to form a compound of formula 9

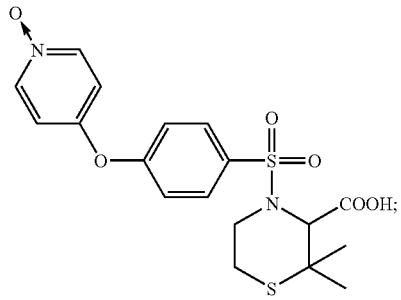

(vii) activating the compound of formula 9 with an activating agent, A₂, to form a compound of formula 10

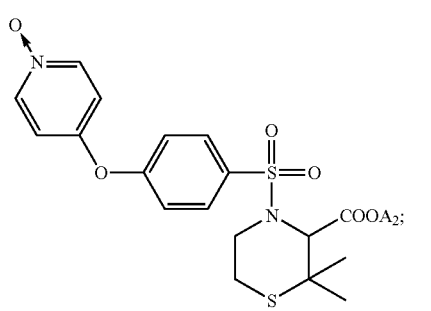

(viii) treating the compound of formula 10 with hydroxylamine to form the compound of formula 11

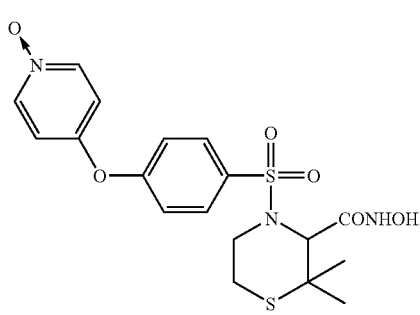

2. A method according to claim 1, wherein the compound of formula 9

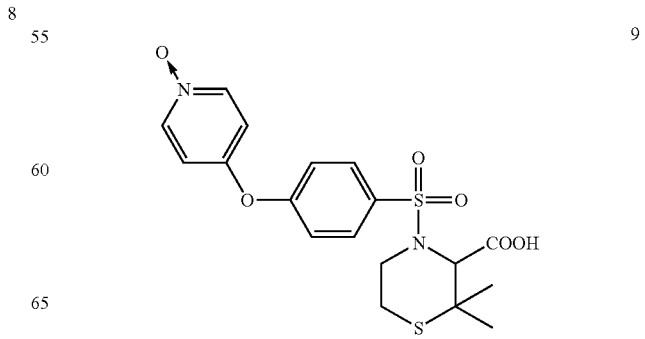

is converted to the compound of formula 11

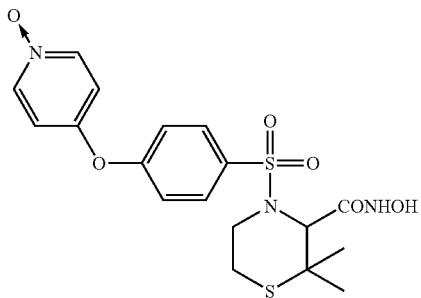

by using an N-protected hydroxylamine and a fluoride based resin as an ion exchanger.

3. A process for synthesizing a compound of formula 22, (3S)-N-hydroxy-4-(4-((1-oxy-pyrid-4-yl)oxy)benzenesulfonyl)-2,2-dimethyl-tetrahydro-2H-1,4-thiazine-3-carboxamide, comprising the steps of:

(i) protecting a compound of formula 12

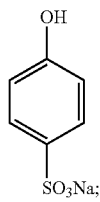

with a protecting group, $P_1$, to form a compound of formula 13

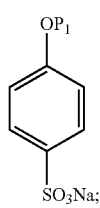

(ii) activating the compound of formula 13 with an activating agent, $A_1$, to form a compound of formula 14

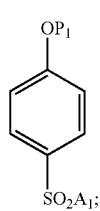

coupling the compound of formula 14 with a compound of formula 15 having an ester, $E_1$

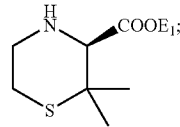

to form a compound of formula 16

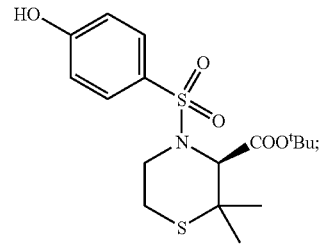

removing the protecting group, $P_1$, from the compound of formula 16 to form a compound of formula 17

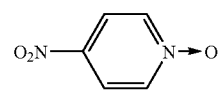

(v) coupling the compound of formula 17 with p-nitro pyridine N-oxide, a compound of formula 18

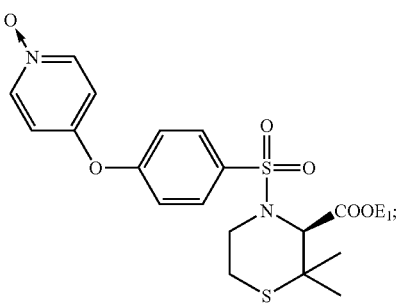

to form a compound of formula 19

(vi) removing the ester, $E_1$, from the compound of formula 19 to form a compound of formula 20

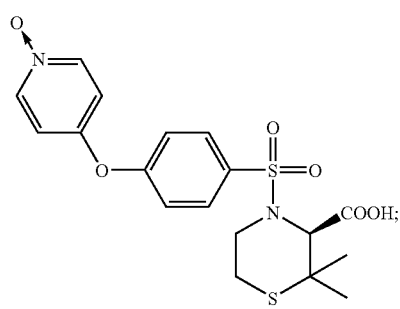

20 activating the compound of formula 20 with an activating agent, $A_2$, to form a compound of formula 21

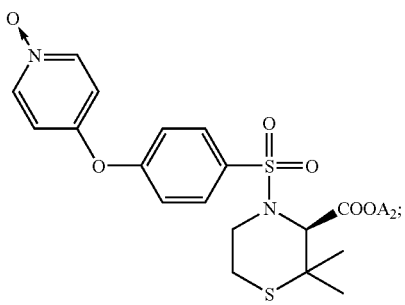

21 treating the compound of formula 21 with hydroxylamine to form the compound of formula 22

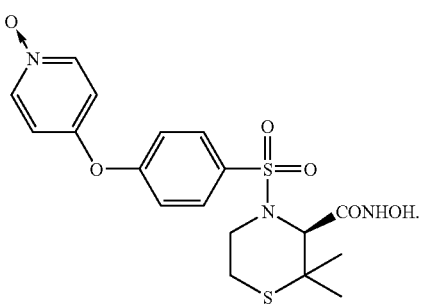

22

4. A method according to claim 3, wherein the compound of formula 20

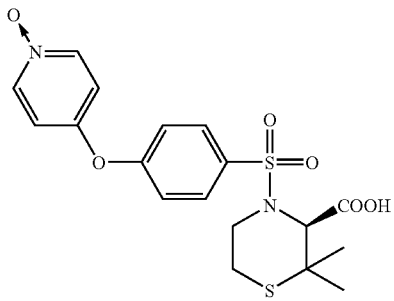

20 is converted to the compound of formula 22

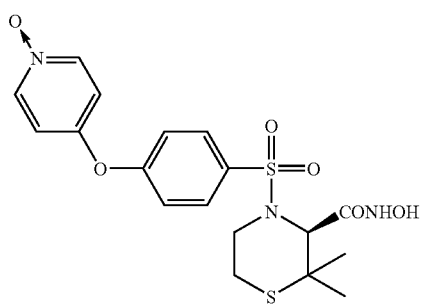

22 by using an N-protected hydroxylamine and a fluoride based resin as an ion exchanger.

5. A method according to claim 1, wherein the phenolic group is protected in said step (i) by treatment with a carboxylic acid anhydride.

6. A method according to claim 5, wherein the carboxylic acid anhydride is acetic anhydride.

7. A method according to claim 6, wherein the pyridine is present during the protection of the phenolic group.

8. A method according to claim 1, wherein the activating agent, $A_1$, in step (ii) is thionyl chloride.

9. A method according to claim 8, wherein said step (ii) is conducted under refluxing conditions.

10. A method according to claim 1, wherein the ester, $E_1$, of 2,2-dimethyl-thiomorpholine-3-carboxylic acid is a tert-butyl ester.

11. A method according to claim 3, wherein the ester, $E_1$, of 2,2-dimethyl-thiomorpholine-3(S)-carboxylic acid is a tert-butyl ester.

12. A method according to claim 1, wherein the protecting group, $P_1$, is removed in said step (vi) by a treatment with potassium carbonate.

13. A method according to claim 12, wherein the potassium carbonate is in aqueous methanol.

14. A method according to claim 1, wherein the coupling in said step (v) is conducted in dimethylformamide.

15. A method according to claim 14, wherein the coupling is conducted in the presence of potassium carbonate.

16. A method according to claim 1, wherein the ester group in said step (vi) is removed by a treatment with a trifluoroacetic acid.

17. A method according to claim 16, wherein the trifluoroacetic acid is in dichloromethane.

18. A method according to claim 17, wherein said step (vi) is conducted in the presence of anisole.

19. A method according to claim 1, wherein the compound of formula 9 or 20 in said step (vii) is activated by a reaction with thionyl chloride.

20. A method according to claim 2, wherein the N-protected hydroxylamine is O-(tert-butyldiphenylsilyl)-hydroxylamine.

21. A method according to claim 2, wherein the fluoride based resin is

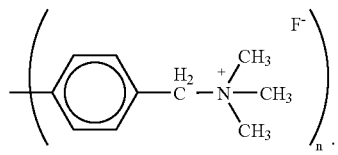

22. A method for synthesizing 2,2-dimethyl-1,1-dioxo-4-[4-(1-oxy-pyridin-4-yloxy)-benzenesulfonyl]-thiomorpholine-3-carboxylic acid amide comprising the steps of:
   (i) converting N-hydroxy-4-(4-((1-oxy-pyrid-4-yl)oxy) benzenesulfonyl)-2,2-dimethyl-tetrahydro-2H-1,4-thiazine-3-carboxamide to a corresponding acid amide; and
   (ii) oxidizing the corresponding acid amide.

23. A method for synthesizing (3S)-2,2-Dimethyl-1,1-dioxo-4-[4-(1-oxy-pyridin-4-yloxy)-benzenesulfonyl]-thiomorpholine-3-carboxylic acid amide comprising the steps of:
   (i) converting (3S)-N-hydroxy-4-(4-((1-oxy-pyrid-4-yl)oxy)benzenesulfonyl)-2,2-dimethyl-tetrahydro-2H-1,4-thiazine-3-carboxamide to a corresponding acid amide; and
   (ii) oxidizing the corresponding acid amide.

24. A method according to claim 22, wherein the corresponding acid amide is oxidized with peracetic acid.

25. A method according to claim 22, wherein the corresponding acid amide is 2,2-dimethyl-4-[4-(1-oxypyridin-4-yloxy)-benzenesulfonyl]-thiomorpholine-3-carboxylic acid amide.

26. A method according to claim 23, wherein the corresponding acid amide is (3S)-2,2-dimethyl-4-[4-(1-oxypyridin-4-yloxy)-benzenesulfonyl]-thiomorpholine-3-carboxylic acid amide.

* * * * *